(12) United States Patent
Huttemann

(10) Patent No.: US 8,241,874 B2
(45) Date of Patent: Aug. 14, 2012

(54) ROLLING CIRCLE AMPLIFICATION

(75) Inventor: Maik Huttemann, Grosse Pointe, MI (US)

(73) Assignee: Wayne State University, Detroit, MI (US)

( * ) Notice: Subject to any disclaimer, the term of this patent is extended or adjusted under 35 U.S.C. 154(b) by 381 days.

(21) Appl. No.: 12/433,703

(22) Filed: Apr. 30, 2009

(65) Prior Publication Data

US 2009/0311698 A1 Dec. 17, 2009

Related U.S. Application Data

(63) Continuation-in-part of application No. 12/190,468, filed on Aug. 12, 2008, now abandoned, which is a continuation of application No. 11/381,653, filed on May 4, 2006, now Pat. No. 7,473,530.

(60) Provisional application No. 60/677,776, filed on May 4, 2005.

(51) Int. Cl.
*C12P 19/34* (2006.01)

(52) U.S. Cl. ....................................................... 435/91.2

(58) Field of Classification Search .................. None
See application file for complete search history.

(56) References Cited

U.S. PATENT DOCUMENTS

| 7,473,530 | B2 | 1/2009 | Huttemann | |
|---|---|---|---|---|
| 2002/0192658 | A1* | 12/2002 | Ward et al. ................ | 435/6 |
| 2003/0104396 | A1* | 6/2003 | Sana et al. ................. | 435/6 |
| 2003/0152932 | A1* | 8/2003 | Kumar et al. .............. | 435/6 |
| 2006/0257898 | A1 | 11/2006 | Huttemann | |

OTHER PUBLICATIONS

Nilsson et al. (2002) Nucleic acid research vol. 30 No. 14 e66.*
Landegren (1993) BioEssays vol. 15 No. 11 pp. 761-765.*
Modrek & Lee (2002) Nature Genetics vol. 30 pp. 13-19.*
Sawai et al. (1994) Journal of the chemical Society, Chemical communications vol. 17 pp. 1997-1998 (abstract of STN search provided).*
Nelson et al. (1989) Nucleic acids res. vol. 17 No. 18 pp. 7179-7186.*
Steinberg et al. (2004) Biopolymers vol. 73:597-605.*
Achilles & Kiedrowski (Feb. 1, 2005) Bioorganic & Medicinal Chemistry Letters vol. 15(4), 1229-1233 (abstract of STN search provided).*
SureLINK Bioconjugation Kit (2005).*
"U.S. Appl. No. 11/381,653, Advisory Action mailed Jan. 29, 2008", 3 pgs.
"U.S. Appl. No. 11/381,653, Final Office Action mailed Sep. 20, 2007", 10 pgs.
"U.S. Appl. No. 11/381,653, Non Final Office Action mailed Feb. 28, 2007", 16 pgs.

(Continued)

*Primary Examiner* — Kenneth R. Horlick
*Assistant Examiner* — Suchira Pande
(74) *Attorney, Agent, or Firm* — Schwegman, Lundberg & Woessner, P.A.

(57) ABSTRACT

A method to detect a messenger ribonucleic acid (mRNA) sequence is provided including annealing a first probe and a second probe to at least a portion of the mRNA, wherein the first and second probes do not comprise the same nucleotide sequence, wherein each probe sequence is complimentary to at least a portion of the mRNA and the second probe is a T-shaped probe having 1) a probe sequence complementary to at least a portion of the mRNA sequence and 2) a rolling circle amplification primer that is linked to an internal reactive group of the probe sequence of the second probe so as to provide physical separation of probe ligation and rolling circle amplification, said probe-connected rolling circle primer comprising a circle recognition sequence.

9 Claims, 6 Drawing Sheets

OTHER PUBLICATIONS

"U.S. Appl. No. 11/381,653, Notice of Allowance mailed Apr. 29, 2008", 4 pgs.
"U.S. Appl. No. 11/381,653, Response filed Jan. 16, 2007 to Restriction Requirement mailed Dec. 13, 2006", 6 pgs.
"U.S. Appl. No. 11/381,653, Response filed Feb. 22, 2008 to Advisory Action mailed Jan. 29, 2008", 7 pgs.
"U.S. Appl. No. 11/381,653, Response filed Jun. 28, 2007 to Non Final Office Action mailed Feb. 28, 2007", 14 pgs.
"U.S. Appl. No. 11/381,653, Response filed Nov. 20, 2007 to Final Office Action mailed Sep. 20, 2007", 15 pgs.
"U.S. Appl. No. 11/381,653, Restriction Requirement mailed 12-13-06", 6 pgs.
"Cancer facts and figures 2002", American Cancer Society, [Online]. Retrieved from the Internet: <URL: http://www.cancer.org/downloads/STT/CancerFacts&Figures2002TM.pdf>, (2002), 1-48.
Acin-Perez, R., et al., "An intragenic suppressor in the cytochrome c oxidase I gene of mouse mitochondrial DNA", Hum Mol Genet., 12(3), (2003), 329-39.
Archer, S., et al., "The mechanism(s) of hypoxic pulmonary vasoconstriction: potassium channels, redox O(2) sensors, and controversies.", News Physiol Sci., 17, (2002), 131-7.
Arnold, S, et al., "The intramitochondrial ATP/ADP-ratio controls cytochrome c oxidase activity allosterically", FEBS Lett., 443(2), (1999), 105-8.
Arnold, S., et al., "3,5-Diiodothyronine binds to subunit Va of cytochrome-c oxidase and abolishes the allosteric inhibition of respiration by ATP", Eur J Biochem., 252(2), (1998), 325-30.
Arnold, S., et al., "Cell respiration is controlled by ATP, an allosteric inhibitor of cytochrome-c oxidase", Eur J Biochem., 249(1), (1997), 350-4.
Avanzo, J. L., et al., "Increased susceptibility to urethane-induced lung tumors in mice with decreased expression of connexin43.", Carcinogenesis, 25(10), (2004), 1973-82.
Barros, R. C., et al., "Hypoxic metabolic response of the golden-mantled ground squirrel", J Appl Physiol., 91(2), (2001), 603-12.
Baty, J. W., et al., "Detection of oxidant sensitive thiol proteins by fluorescence labeling and two-dimensional electrophoresis", Proteomics, 2(9), (2002), 1261-6.
Bender, E., et al., "The allosteric ATP-inhibition of cytochrome c oxidase activity is reversibly switched on by cAMP-dependent phosphorylation.", FEBS Lett., 466(1), (2000), 130-4.
Boehle, A. S., et al., "Wortmannin inhibits growth of human non-small-cell lung cancer in vitro and in vivo", Langenbecks Arch Surg., 387(5-6), (2002), 234-9.
Boerner, J. L., et al., "Phosphorylation of Y845 on the epidermal growth factor receptor mediates binding to the mitochondrial protein cytochrome c oxidase subunit II.", Mol Cell Biol., 24(16), (2004), 7059-71.
Brand, M. D., et al., "Stimulation of the electron transport chain in mitochondria isolated from rats treated with mannoheptulose or glucagon", Arch Biochem Biophys., 283(2), (1990), 278-84.
Burgess, J. W., et al., "cAMP-dependent protein kinase isozymes with preference for histone H2B as substrate in mitochondria of bovine heart.", Biochem Cell Biol., 65(2), (1987), 137-43.
Burke, P. V., et al., "Structure/function of oxygen-regulated isoforms in cytochrome c oxidase", J Exp Biol., 201(Pt 8), (1998), 1163-75.
Cantley, L. C., "The phosphoinositide 3-kinase pathway.", Science, 296(5573), (2002), 1655-7.
Cardone, L., et al., "Mitochondrial AKAP121 binds and targets protein tyrosine phosphatase D1, a novel positive regulator of src signaling.", Mol Cell Biol., 24(11), (2004), 4613-26.
Chandel, N. S., et al., "Cellular oxygen sensing by mitochondria: old questions, new insight.", J Appl Physiol., 88(5), (2000), 1880-9.
Chandel, N. S., et al., "Mitochondrial reactive oxygen species trigger hypoxia-induced transcription", Proc Natl Aced Sci U S A., 95(20), (1998), 11715-20.
Chen, R., et al., "The phosphorylation of subunits of complex I from bovine heart mitochondria", J Biol Chem., 279(25), (2004), 26036-45.
Corso, M., et al., "Protein phosphorylation in mitochondria from human placenta", Placenta, 22(5), (2001), 432-9.

Cuezva, J. M., et al., "Mitochondrial biogenesis in the liver during development and oncogenesis.", J Bioenerg Biomembr., 29(4), (1997), 365-77.
Cumsky, M. G., et al., "Structural analysis of two genes encoding divergent forms of yeast cytochrome c oxidase subunit V.", Mol Cell Biol., 7(10), (1987), 3511-9.
Dal Piaz, V., et al., "Phosphodiesterase 4 inhibitors, structurally unrelated to rolipram, as promising agents for the treatment of asthma and other pathologies.", Eur J Med Chem., 35(5), (2000), 463-80.
Dignam, J. D., et al., "Accurate transcription initiation by RNA polymerase II in a soluble extract from isolated mammalian nuclei.", Nucleic Acids Res., 11(5), (1983), 1475-89.
Dimino, M. J., et al., "Cyclic AMP-dependent protein kinase in mitochondria and cytosol from different-sized follicles and corpora lutea of porcine ovaries.", J Biol Chem., 256(21), (1981), 10876-82.
Eng, J. K., et al., "An approach to correlate tandem mass spectral data of peptides with amino acid sequences in a protein database", Journal of the American Society for Mass Spectrometry, 5, (1994), 976-989.
Epstein, M. A., et al., "A theoretical analysis of the barometric method for measurement of tidal volume", Respir Physiol., 32(1), (1978), 105-20.
Esamai, F. O., et al., "Relationship between exposure to tobacco smoke and bronchial asthma in children: a review", East Afr Med J., 75(1), (1998), 47-50.
Ferguson-Miller, S., et al., "Correlation of the kinetics of electron transfer activity of various eukaryotic cytochromes c with binding to mitochondrial cytochrome c oxidase.", J Biol Chem., 251(4), (1976), 1104-15.
Ferguson-Miller, S., et al., "Definition of cytochrome c binding domains by chemical modification. III. Kinetics of reaction of carboxydinitrophenyl cytochromes c with cytochrome c oxidase", J Biol Chem., 253(1), (1978), 149-59.
Frank, V., et al., "Regulation of the H+/e- stoichiometry of cytochrome c oxidase from bovine heart by intramitochondrial ATP/ADP ratios.", FEBS Lett., 382(1-2), (1996), 121-4.
Frohrnan, M. A., "", PCR Primer, A Laboratorial Manual, Dieffenbach, C. W., and Dveksler, G. S., Eds., Cold Spring Harbor Laboratory Press, Cold Spring Harbor, NY, (1995), 381-409.
Garber, E. A., et al., "Interaction of cytochrome c with cytochrome c oxidase: an understanding of the high- to low-affinity transition.", Biochim Biophys Acta., 1015(2), (1990), 279-87.
Gnaiger, E., et al., "Mitochondrial oxygen affinity, respiratory flux control and excess capacity of cytochrome c oxidase", J Exp Biol., 201(Pt 8), (1998), 1129-39.
Green, R. H., et al., "Management of asthma in adults: current therapy and future directions", Postgrad Med J., 79(931), (2003), 259-67.
Griffioen, G., et al., "Molecular mechanisms controlling the localisation of protein kinase A.", Curr Genet., 41(4), (2002), 199-207.
Grossman, L. I., et al., "Nuclear genes for cytochrome c oxidase.", Biochim Biophys Acta., 1352(2), (1997), 174-92.
Gyuris, J., et al., "Cdi1, a human G1 and S phase protein phosphatase that associates with Cdk2", Cell, 75(4), (1993), 791-803.
Heinemeyer, T., et al., "Databases on transcriptional regulation: TRANSFAC, TRRD and COMPEL.", Nucleic Acids Res., 26(1), (1998), 362-7.
Hirsch, F. R., et al., "Prevention and early detection of lung cancer-clinical aspects.", Lung Cancer, 17(1), (1997), 163-74.
Huttemann, M., et al., "A third isoform of cytochrome c oxidase subunit VIII is present in mammals", Gene, 312, (2003), 95-102.
Huttemann, M., et al., "Cytochrome c oxidase of mammals contains a testes-specific isoform of subunit VIb—the counterpart to testes-specific cytochrome c?", Mol Reprod Dev., 66(1), (2003), 8-16.
Huttemann, M., et al., "Mammalian subunit IV isoforms of cytochrome c oxidase", Gene, 267(1), (2001), 111-23.
Huttemann, M., "Partial heat denaturation step during reverse transcription and PCR screening yields full-length 5'-cDNAs", Biotechniques, 32(4), (2002), 730,732,734,736.
Jaakkola, Panu, "Targeting of HIF-alpha to the von Hippel-Lindau Ubiquitylation Complex by O2-Regulated Prolyl Hydroxylation", Science, 292(5516), (2001), 468-472.

Jackson, S. P., et al., "GC box binding induces phosphorylation of Sp1 by a DNA-dependent protein kinase", Cell, 63(1), (1990), 155-65.

Jacky, J. P., "Barometric measurement of tidal volume: effects of pattern and nasal temperature", J Appl Physiol., 49(2), (1980), 319-25.

Jiang, F., et al., "Absence of cardiolipin in the crd1 null mutant results in decreased mitochondrial membrane potential and reduced mitochondrial function.", J Biol Chem., 275(29), (2000), 22387-94.

Joad, J. P., et al., "Passive smoke effects on cough and airways in young guinea pigs: role of brainstem substance P", Am J Respir Crit Care Med., 169(4), (2004), 499-504.

Kadenbach, B., et al., "Isozymes of cytochrome-c oxidase: characterization and isolation from different tissues", Methods Enzymol., 126, (1986), 32-45.

Kadenbach, B., et al., "Regulation of mitochondrial energy generation in health and disease", Biochim Biophys Acta, 1271, (1995), 103-9.

Kadenbach, B., et al., "Separation of mammalian cytochrome c oxidase into 13 polypeptides by a sodium dodecyl sulfate-gel electrophoretic procedure", Anal Biochem., 129, (1983), 517-21.

Kadenbach, Bernhard, et al., "The possible role of cytochrome c oxidase in stress-induced apoptosis and degenerative diseases", Biochimica et Biophysics Acta 1655, (2004), 400-408.

King, M. P., et al., "Human cells lacking mtDNA: repopulation with exogenous mitochondria by complementation", Science, 246(4929), (1989), 500-3.

Kleitke, B., et al., "Evidence for cyclic AMP-dependent protein kinase activity in isolated guinea pig and rat liver mitochondria.", Acta Biol Med Ger., 35(3-4), (1976), K9-K17.

Kolonin, M. G., et al., "Interaction mating methods in two-hybrid systems", Methods Enzymol., 328, (2000), 26-46.

Kondrashin, A. A., et al., "Subcellular distribution of the R-subunits of cAMP-dependent protein kinase in LS-174T human colon carcinoma cells.", Biochem Mol Biol Int., 45(2), (1998), 237-44.

Korshunov, S. S., et al., "High protonic potential actuates a mechanism of production of reactive oxygen species in mitochondria.", FEBS Lett., 416(1), (1997), 15-8.

Kosower, N. S., et al., "Diamide: an oxidant probe for thiols", Methods Enzymol., 251, (1995), 123-33.

Lando, D., et al., "Asparagine hydroxylation of the HIF transactivation domain a hypoxic switch", Science, 295(5556), (2002), 858-61.

Lee, I., et al., "Control of mitochondrial membrane potential and ROS formation by reversible phosphorylation of cytochrome c oxidase", Mol Cell Biochem., 234-235(1-2), (2002), 63-70.

Lee, I., et al., "New control of mitochondrial membrane potential and ROS formation—a hypothesis", Biol Chem., 382(12), (2001), 1629-36.

Lee, I., et al., "Palmitate decreases proton pumping of liver-type cytochrome c oxidase", Eur J Biochem., 268(24), (2001), 6329-34.

Li, J., et al., "Lung pathology in platelet-derived growth factor transgenic mice: effects of genetic background and fibrogenic agents.", Exp Lung Res., 28(6), (2002), 507-22.

Licklider, L. J., et al., "Automation of Nanoscale Microcapillary Liquid Chromatography-Tandem Mass Spectrometry with a Vented Column", Analytical Chemistry, 74(13), (2002), 3076-3083.

Lin, X., et al., "Overexpression of phosphatidylinositol 3-kinase in human lung cancer", Langenbecks Arch Surg., 386(4), (2001), 293-301.

Lundblad, L. K., et al., "A reevaluation of the validity of unrestrained plethysmography in mice", J Appl Physiol., 93(4), (2002), 1198-207.

Malkinson, A. M., "The genetic basis of susceptibility to lung tumors in mice", Toxicology, 54(3), (1989), 241-71.

Manning, G., et al., "The Protein Kinase Complement of the Human Genome", Science, 298(5600), (2002), 1912-1934.

Michelakis, E. D., et al., "Diversity in mitochondrial function explains differences in vascular oxygen sensing", Circ Res., 90(12), (2002), 1307-15.

Miller, Y. E., et al., "Induction of a high incidence of lung tumors in C57BL/6 mice with multiple ethyl carbamate injections.", Cancer Lett., 198(2), (2003), 139-44.

Miyazaki, T., et al., "Regulation of cytochrome c oxidase activity by c-Src in osteoclasts", J Cell Biol., 160(5), (2003), 709-18.

Muller, G., et al., "Protein phosphorylation in yeast mitochondria: cAMP-dependence, submitochondrial localization and substrates of mitochondrial protein kinases.", Yeast, 3(3), (1987), 161-74.

Napiwotzki, J., et al., "ATP and ADP bind to cytochrome c oxidase and regulate its activity", Biol Chem., 378(9), (1997), 1013-21.

Ng, P. S., et al., "Protein-DNA footprinting by endcapped duplex oligodeoxyribonucleotides", Nucleic Acids Res., 32(13), (2004), e107.

Nilsson, M., et al., "Real-time monitoring of rolling-circle amplification using a modified molecular beacon design", Nucleic Acids Res., 30(14), (2002), e66.

Ortega-Saenz, P., et al., "Rotenone selectively occludes sensitivity to hypoxia in rat carotid body glomus cells", J Physiol., 548(Pt 3), (2003), 789-800.

Osheroff, N., et al., "The reaction of primate cytochromes c with cytochrome c oxidase. Analysis of the polarographic assay.", J Biol Chem., 258(9), (1983), 5731-8.

Paddenberg, R., et al., "Essential role of complex II of the respiratory chain in hypoxia-induced ROS generation in the pulmonary vasculature.", Am J Physiol Lung Cell Mol Physiol., 284(5), (2003), L710-9.

Papa, S., et al., "cAMP-dependent protein kinase and phosphoproteins in mammalian mitochondria. An extension of the cAMP-mediated intracellular signal transduction", FEBS Lett., 444(2-3), (1999), 245-9.

Pariset, C., et al., "Differential localization of two isoforms of the regulatory subunit RII alpha of cAMP-dependent protein kinase in human sperm: biochemical and cytochemical study", Mol Reprod Dev., 39(4), (1994), 415-22.

Pedersen, P. L., "Tumor mitochondria and the bioenergetics of cancer cells", Prog Exp Tumor Res., 22, (1978), 190-274.

Pohl, S. L., et al., "The glucagon-sensitive adenyl cyclase system in plasma membranes of rat liver. I. Properties", J Biol Chem., 246(6), (1971), 1849-56.

Robb-Gaspers, L. D., et al., "Integrating cytosolic calcium signals into mitochondrial metabolic responses", EMBO J., 17(17), (1998), 4987-5000.

Robinson-White, A., et al., "Protein kinase A signaling: "cross-talk" with other pathways in endocrine cells", Ann N Y Acad Sci., 968, (2002), 256-70.

Rodriguez-Enriquez, S., et al., "Intermediary metabolism of fast-growth tumor cells", Arch Med Res., 29(1), (1998), 1-12.

Rutter, J., et al., "Regulation of clock and NPAS2 DNA binding by the redox state of NAD cofactors", Science, 293(5529), (2001), 510-4.

Ryan, J., et al., "KRAS2 as a genetic marker for lung tumor susceptibility in inbred mice", J Natl Cancer Inst., 79(6), (1987), 1351-7.

Santillan, A. A., et al., "A meta-analysis of asthma and risk of lung cancer (United States).", Cancer Causes Control, 14(4), (2003), 327-34.

Schroedl, C., et al., "Hypoxic but not anoxic stabilization of HIF-1alpha requires mitochondrial reactive oxygen species", Am J Physiol Lung Cell Mol Physiol., 283(5), (2002), L922-31.

Schuller, H. M., et al., "Neuroendocrine lung carcinogenesis in hamsters is inhibited by green tea or theophylline while the development of adenocarcinomas is promoted: implications for chemoprevention in smokers", Lung Cancer, 45(1), (2004), 11-8.

Semenza, G. L., "HIF-1 and human disease: one highly involved factor", Genes Dev., 14(16), (2000), 1983-91.

Shoelson, S. E., et al., "Tryptic activation of the insulin receptor. Proteolytic truncation of the alpha-subunit releases the beta-subunit from inhibitory control.", J Biol Chem., 263(10), (1988), 4852-60.

Siddiq, F., et al., "Increased osteonectin expression is associated with malignant transformation and tumor associated fibrosis in the lung.", Lung Cancer, 45(2), (2004), 197-205.

Sodhi, C. P., et al., "Hypoxia and high glucose cause exaggerated mesangial cell growth and collagen synthesis: role of osteopontin.", Am J Physiol Renal Physiol., 280(4), (2001), F667-74.

Speck, S. H., et al., "Single catalytic site model for the oxidation of ferrocytochrome c by mitochondrial cytochrome c oxidase.", Proc Natl Acad Sci U S A., 81(2), (1984), 347-51.

Steenaart, N. A., et al., "Mitochondrial cytochrome c oxidase subunit IV is phosphorylated by an endogenous kinase", FEBS Lett., 415(3), (1997), 294-8.

Suarez, M. D., et al., "The functional and physical form of mammalian cytochrome c oxidase determined by gel filtration, radiation inactivation, and sedimentation equilibrium analysis.", J Biol Chem., 259(22), (1984), 13791-9.

Suh, Y. A., et al., "Cell transformation by the superoxide-generating oxidase Mox1", Nature, 401(6748), (1999), 79-82.

Technikova-Dobrova, Z., et al., "Cyclic adenosine monophosphate-dependent phosphorylation of mammalian mitochondrial proteins: enzyme and substrate characterization and functional role", Biochemistry, 40(46), (2001), 13941-7.

Tockman, M. S., et al., "Considerations in Bringing a Cancer Biomarker to Clinical Application", Cancer Research (Suppl.), 52, (May 1, 1992), 2711s-2718s.

Tsukihara, T., et al., "The low-spin heme of cytochrome c oxidase as the driving element of the proton-pumping process", Proc Natl Acad Sci U S A., 100(26), (2003), 15304-9.

Tsukihara, T., et al., "The whole structure of the 13-subunit oxidized cytochrome c oxidase at 2.8 A", Science, 272(5265), (1996), 1136-44.

Vaupel, P., et al., "Blood flow, oxygen and nutrient supply, and metabolic microenvironment of human tumors: a review.", Cancer Res., 49(23), (1989), 6449-65.

Villani, G., et al., "Low reserve of cytochrome c oxidase capacity in vivo in the respiratory chain of a variety of human cell types.", J Biol Chem., 273(48), (1998), 31829-36.

Von Wangenheim, K. H., et al., "Control of cell proliferation by progress in differentiation: clues to mechanisms of aging, cancer causation and therapy.", J Theor Biol., 193(4), (1998), 663-78.

Ward, J. P., "Mitochondria and oxygen sensing: fueling the controversy", J Physiol., 548(Pt 3), (2003), 664.

Waypa, G. B., et al., "Mitochondrial reactive oxygen species trigger calcium increases during hypoxia in pulmonary arterial myocytes.", Circ Res., 91(8), (2002), 719-26.

Waypa, G. B., et al., "Model for hypoxic pulmonary vasoconstriction involving mitochondrial oxygen sensing", Circ Res., 88(12), (2001), 1259-66.

Wong-Riley, M., "Changes in the visual system of monocularly sutured or enucleated cats demonstrable with cytochrome oxidase histochemistry.", Brain Res., 171(1), (1979), 11-28.

Yamamoto, K., et al., "Fluorometric studies on the light chains of skeletal muscle myosin. I. Effects of temperature, ionic strength, divalent metal ions, and nucleotides.", J Biochem (Tokyo), 82(3), (1977), 747-52.

You, M., et al., "Parental bias of Ki-ras oncogenes detected in lung tumors from mouse hybrids", Proc Natl Acad Sci U S A., 89(13), (1992), 5804-8.

Yu, A. Y., et al., "Temporal, spatial, and oxygen-regulated expression of hypoxia-inducible factor-1 in the lung", Am J Physiol., 275(4 Pt 1), (1998), L818-26.

Yu, M., et al., "Genomic organization and promoter regulation of human cytochrome c oxidase subunit VII heart/muscle isoform (COX7AH).", Biochim Biophys Acta., 1574(3), (2002), 345-53.

Zhang, Q., et al., "Regulation of corepressor function by nuclear NADH", Science, 295(5561), (2002), 1895-7.

Zhao, Y., et al., "Effect of cytochrome c on the generation and elimination of O2- and H2O2 in mitochondria", J Biol Chem., 278(4), (2003), 2356-60.

Zhong, J., et al., "A strategy for constructing large protein interaction maps using the yeast two-hybrid system: regulated expression arrays and two-phase mating", Genome Res., 13(12), (2003), 2691-9.

Larsson, C., et al., "In situ detection and genotyping of individual mRNA molecules", Nat Methods., 7(5), (May 2010), 395-7.

* cited by examiner

SEQUENCE LISTING

```
<160> NUMBER OF SEQ ID NOS: 11

<210> SEQ ID NO 1
<211> LENGTH: 29
<212> TYPE: DNA
<213> ORGANISM: Homo sapiens

<400> SEQUENCE: 1
tacgagctca tgaaagtgtt gtgaagagc                                            29
```

```
<210> SEQ ID NO 2
<211> LENGTH: 19
<212> TYPE: DNA
<213> ORGANISM: Homo sapiens

<400> SEQUENCE: 2
gaagactttt cgctcccag                                                  19

<210> SEQ ID NO 3
<211> LENGTH: 29
<212> TYPE: DNA
<213> ORGANISM: Homo sapiens

<400> SEQUENCE: 3
ttggtggcag cgggtctacg tatttcctc                                       29

<210> SEQ ID NO 4
<211> LENGTH: 18
<212> TYPE: DNA
<213> ORGANISM: Homo sapiens

<400> SEQUENCE: 4
caaagccgat caccttga                                                   18

<210> SEQ ID NO 5
<211> LENGTH: 100
<212> TYPE: DNA
<213> ORGANISM: Artificial Sequence
<220> FEATURE:
<223> OTHER INFORMATION: A synthetic oligonucleotide

<400> SEQUENCE: 5
cctgccctgc gaattcgggt atagtgagtt aaattcatag gaaacaccaa agatgatatt     60
tgctcggata catatttagt gacactatag cgagccgagc                          100

<210> SEQ ID NO 6
<211> LENGTH: 28
<212> TYPE: DNA
<213> ORGANISM: Artificial Sequence
<220> FEATURE:
<223> OTHER INFORMATION: A synthetic oligonucleotide

<400> SEQUENCE: 6
gctcggatac atatttagtg acactata                                        28

<210> SEQ ID NO 7
<211> LENGTH: 50
<212> TYPE: DNA
<213> ORGANISM: Artificial Sequence
<220> FEATURE:
<223> OTHER INFORMATION: A synthetic oligonucleotide

<400> SEQUENCE: 7
aactaaccaa tcagttcgct tctcgctttt gcagggcagg gctcggctcg                50

<210> SEQ ID NO 8
<211> LENGTH: 9
<212> TYPE: DNA
<213> ORGANISM: Artificial Sequence
<220> FEATURE:
<223> OTHER INFORMATION: A synthetic oligonucleotide

<400> SEQUENCE: 8 cgctcccag                                                              9
```

```
<210> SEQ ID NO 9
<211> LENGTH: 29
<212> TYPE: DNA
<213> ORGANISM: Artificial Sequence
<220> FEATURE:
<223> OTHER INFORMATION: A synthetic oligonucleotide

<400> SEQUENCE: 9
tacgagctca tgaaagtgtt gtgaagagc                                    29

<210> SEQ ID NO 10
<211> LENGTH: 9
<212> TYPE: DNA
<213> ORGANISM: Artificial Sequence
<220> FEATURE:
<223> OTHER INFORMATION: A synthetic oligonucleotide

<400> SEQUENCE: 10 caaagccga                                                           9

<210> SEQ ID NO 11
<211> LENGTH: 29
<212> TYPE: DNA
<213> ORGANISM: Artificial Sequence
<220> FEATURE:
<223> OTHER INFORMATION: A synthetic oligonucleotide

<400> SEQUENCE: 11
ttggtggcag cgggtctacg tatttcctc                                    29
```

ROLLING CIRCLE AMPLIFICATION

RELATED APPLICATIONS

This application is a continuation-in-part of U.S. application Ser. No. 12/190,468, filed Aug. 12, 2008 which is a continuation under 37 C.F.R. 1.53(b) of U.S. application Ser. No. 11/381,653, filed May 4, 2006, now U.S. Pat. No. 7,473,530 which claims priority under 35 U.S.C. 119(e) from U.S. Provisional Patent Application Ser. No. 60/677,776, filed on May 4, 2005, the contents of which are incorporated herein by reference in their entirety.

FIELD OF THE INVENTION

Certain embodiments of the present invention relate to methods for detecting DNA or RNA (including, but not limited to, mRNA).

BACKGROUND OF THE INVENTION

Lung cancer is the leading cause of cancer death and accounts for nearly 30% of all cancer deaths in the United States, and there is an increasing incidence of lung cancer in the world. The overall 5-year survival rate of patients with lung cancer has not improved significantly over the last 30 years and remains at only 10-15% in the United States. The prognosis of patients with lung cancer depends in large part on the stage of presentation when the lung cancer is diagnosed. Thus, early detection of lung cancer in conjunction with early treatment would be expected to significantly reduce mortality from lung cancer.

Accordingly, there is a need for methods for detecting lung cancer, e.g., methods for detecting lung cancer at an early stage of presentation.

SUMMARY OF CERTAIN EMBODIMENTS OF THE INVENTION

It has been discovered that the COX4-2 isoform of cytochrome c oxidase (COX) is a highly significant marker for lung cancer as downregulation of the COX4-2 gene is indicative of the presence of lung cancer.

Accordingly, certain embodiments of the present invention provide a method for detecting the presence of lung cancer in a first biological sample, including determining the level of isoform 2 of subunit 4 of cytochrome c oxidase (COX4-2) in the first biological sample, wherein a lower level of COX4-2 in the first biological sample as compared to the level of COX4-2 in a second biological sample that does not include lung cancer indicates the presence of lung cancer in the first biological sample.

Certain embodiments of the present invention provide a method for screening a subject at an elevated risk for developing lung cancer, including determining the level of isoform 2 of subunit 4 of cytochrome c oxidase (COX4-2) in a biological sample from the subject, wherein a lower level of COX4-2 in the sample as compared to the level of COX4-2 in a biological sample that does not include lung cancer indicates the that the subject has lung cancer.

Certain embodiments of the present invention provide a method for identifying and treating lung cancer in a subject, including determining the level of isoform 2 of subunit 4 of cytochrome c oxidase (COX4-2) in a biological sample from the subject, wherein a lower level of COX4-2 in the sample as compared to the level of COX4-2 in a biological sample that does not include lung cancer indicates the that the subject has lung cancer, and administering a treatment for lung cancer to the patient.

Certain embodiments of the present invention provide a method for determining whether a subject has lung cancer, including determining the level of isoform 2 of subunit 4 of cytochrome c oxidase (COX4-2) in a biological sample from the subject, wherein a lower level of COX4-2 in the sample as compared to the level of COX4-2 in a biological sample that does not include lung cancer indicates the that the subject has developed lung cancer.

In certain embodiments of the invention, the methods may further include determining the level of isoform 1 of subunit 4 of cytochrome c oxidase (COX4-1) in a sample and comparing the level of COX4-2 to COX4-1, wherein a lower ratio of COX4-1 to COX4-2 indicates the presence of lung cancer in the sample.

One embodiment provides a method to detect a messenger ribonucleic acid (mRNA) sequence comprising: a) annealing a first probe and a second probe to at least a portion of the mRNA, wherein the first and second probes do not comprise the same nucleotide sequence, wherein each probe sequence is complimentary to at least a portion of the mRNA and the second probe comprises a stem nucleotide sequence linked to an internal reactive group (e.g., an amine group; as used herein, "reactive group" includes a moiety on the compound that is capable of chemically reacting with a functional group on a different compound to form a covalent linkage. Typically the reactive group is an electrophile or nucleophile that can form a covalent linkage through exposure to the corresponding functional group that is a nucleophile or electrophile, respectively) of the second probe, said stem sequence comprising a circle recognition sequence; b) concatenating the two annealed probes with a ligase to yield a ligated annealed probe and removing unligated probe from the mRNA sequence; c) annealing a single stranded amplification circle to the circle recognition sequence of the ligated probe, wherein the single stranded amplification circle codes for a recognition sequence for an oligonucleotide to which a fluorophore is attached (e.g., the oligonucleotide with the fluorophore is complementary to the recognition sequence and a capable of hybridizing to it); d) generating a plurality of copies of the oligonucleotide recognition sequence with a strand replacement polymerase; e) annealing the oligonucleotide to at least one of the oligonucleotide recognition sequences; and f) detecting the presence of the fluorophore, wherein the presence of the fluorophore correlates with the presence of the mRNA.

BRIEF DESCRIPTION OF THE FIGURES

This patent document contains at least one drawing executed in color. Copies of this patent document with color drawing(s) will be provided by the Office upon request and payment of the necessary fee.

DETAILED DESCRIPTION OF CERTAIN EMBODIMENTS OF THE INVENTION

Figure 1:
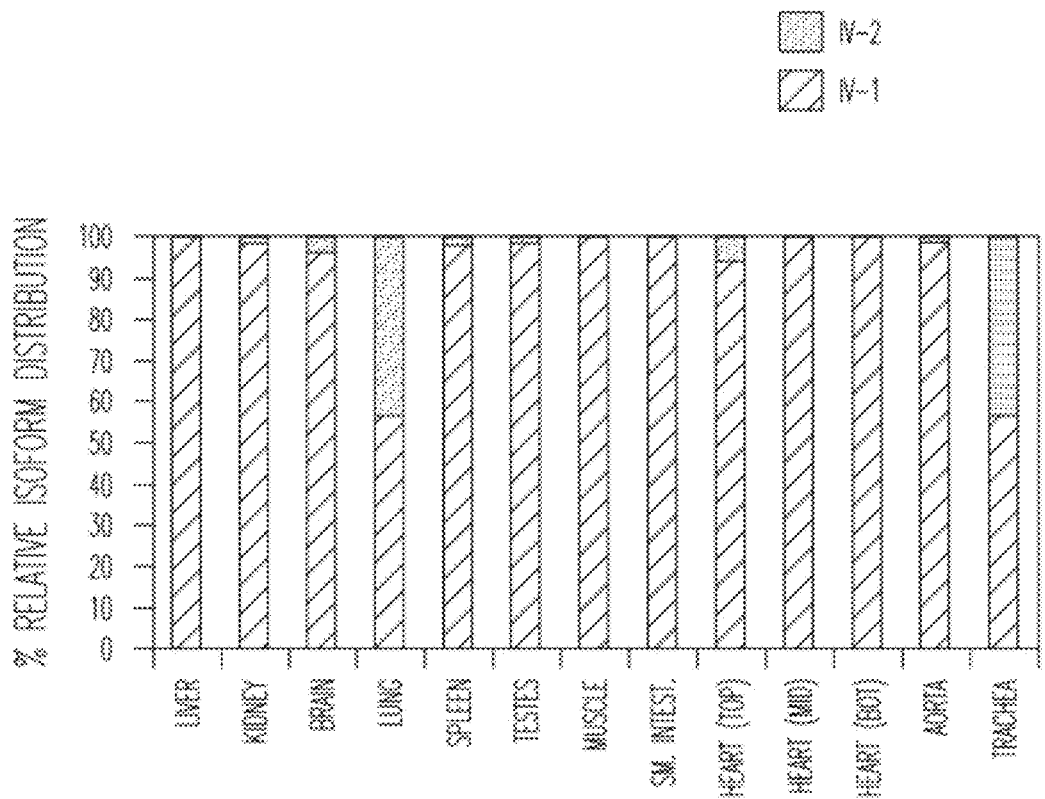
FIG. 1. Relative quantitative PCR of cytochrome c oxidase subunit isoforms 4-1 and 4-2 reveals strong expression in lung and trachea.

COX is the rate-limiting enzyme of the mitochondrial respiratory chain that provides humans with the vast majority of their energy requirements. Consistent with its position as a pacemaker of aerobic metabolism, the activity of COX is tightly regulated through several means, including tissue-specific isoforms. As described herein, it is this form of regulation that is directly relevant to lung cancer because of the existence of two isoforms of subunit 4 of COX.

COX 4 is the key regulatory subunit of COX that adjusts enzyme activity to meet cellular energy demand. The gene encoding the lung-specific isoform, COX4-2, is switched on after birth and is expressed in all cell types of the lung. Presented herein are studies that indicate that expression of the COX4-2 gene is dramatically downregulated in lung cancer, whereas expression of the somatic isoform of the gene, COX4-1, is at normal levels. This finding is consistent for various types of lung cancer and lung cancer cell lines, including a cell culture model simulating the carcinogenesis process in vivo, where COX4-2 is downregulated from the earliest stages.

The data presented herein thus indicates that COX4-2 is a highly significant early marker for lung cancer. The surprising finding that COX4-2 is an important lung cancer marker has been examined by using TaqMan real time PCR on lung cancers from various stages and matching controls derived from smokers. A new diagnostic assay based on probe ligation and rolling circle amplification (RCA) is also described herein, which assay will allow for the detection of COX4-2 expression, e.g., in individual cells, e.g., in sputum, saliva, bronchoalveolar lavage (BAL), bronchoscopy, biopsy, and tissue section samples. COX4-1, the ubiquitously expressed paralogue, can serve as an internal standard. The use of COX4-2 as an early lung cancer marker allow for non-invasive early lung cancer detection. Such a system will be especially valuable for screening high-risk populations e.g., people who smoke, for the development of lung cancer.

As an early biomarker of the changes ensuing upon the beginning of lung cancer, COX4-2 mRNA and/or protein are useful markers for the early diagnosis of lung cancer. Moreover, the robust, non-invasive, assay described herein will be generalizable to the detection of other biomarkers using biological samples such as bronchoalveolar lavage (BAL), sputum, blood, or cell smear samples. The assay provides a novel way to easily and quickly distinguish with great specificity and ease of visualization the differential expression of two or more genes within an individual cell. The assay will provide the ease of use, specificity, and robustness important for the routine use of a diagnostic test. Until now, such tests have generally been of the in situ hybridization type, are excessively complex, lack specificity, and are time consuming. Thus, also provided are kits for performing the assays of the invention that include materials for specifically determining the expression of at least one gene within an individual cell, e.g., for specifically determining the differential expression of two or more genes within an individual cell.

The diagnostic assays described herein will also remove what is at the present time a large obstacle to successful treatment of lung cancer with extant therapeutic measures: the condition generally is not diagnosed sufficiently early. The switch from expression of COX4-2 to COX4-1 in lung cancer means that the expression/nonexpression of the COX4-2 gene provides a specific biomarker for the transition to lung cancer, and is thus an example of a sensitive, specific biomarker to diagnose lung cancer.

Accordingly, certain embodiments of the present invention provide methods for detecting the presence of lung cancer in a first biological sample, including determining the level of isoform 2 of subunit 4 of cytochrome c oxidase (COX4-2) in the first biological sample, wherein a lower level of COX4-2 in the first biological sample as compared to the level of COX4-2 in a second biological sample that does not include lung cancer indicates the presence of lung cancer in the first biological sample.

Certain embodiments of the present invention provide methods for screening a subject at an elevated risk for developing lung cancer, including determining the level of isoform 2 of subunit 4 of cytochrome c oxidase (COX4-2) in a biological sample from the subject, wherein a lower level of COX4-2 in the sample as compared to the level of COX4-2 in a biological sample that does not include lung cancer indicates the that the subject has lung cancer.

Certain embodiments of the present invention provide methods for identifying and treating lung cancer in a subject, including determining the level of isoform 2 of subunit 4 of cytochrome c oxidase (COX4-2) in a biological sample from the subject, wherein a lower level of COX4-2 in the sample as compared to the level of COX4-2 in a biological sample that does not include lung cancer indicates the that the subject has lung cancer, and administering a treatment for lung cancer to the patient.

Certain embodiments of the present invention provide methods for determining whether a subject has lung cancer, including determining the level of isoform 2 of subunit 4 of cytochrome c oxidase (COX4-2) in a biological sample from the subject, wherein a lower level of COX4-2 in the sample as compared to the level of COX4-2 in a biological sample that does not include lung cancer indicates the that the subject has developed lung cancer.

In certain embodiments of the present invention, the first biological sample is obtained from a subject who is at an elevated risk for developing lung cancer. In certain embodiments of the present invention, the subject is at an elevated risk for developing lung cancer. In certain embodiments of the present invention, the subject has a history of smoking at least one form of a tobacco product. In certain embodiments of the present invention, the subject has a history of exposure to second-hand smoke. In certain embodiments of the present invention, the subject has a genetic predisposition for developing lung cancer. In certain embodiments of the present invention, the subject has a history of exposure to asbestos fibers. In certain embodiments of the present invention, the subject has a history of exposure to elevated levels of radon.

In certain embodiments of the present invention, the biological samples include sputum. In certain embodiments of the present invention, the biological samples include saliva. In certain embodiments of the present invention, the biological samples are obtained using bronchoalveolar lavage. In certain embodiments of the present invention, the biological samples include a biopsy sample of lung tissue.

In certain embodiments of the present invention, the level of COX4-2 and/or COX4-1 is determined by measuring the amount of COX4-2 mRNA and/or COX4-1 mRNA. In certain embodiments of the present invention, the level of COX4-2 and/or COX4-1 is determined by measuring the amount of COX4-2 and/or COX4-1 protein.

In certain embodiments of the present invention, the level of COX4-2 and/or COX4-1 is measured in a single cell.

In certain embodiments of the present invention, the treatment includes surgery, chemotherapy, radiation therapy, a targeted therapy, immunotherapy, or a combination thereof. In certain embodiments of the present invention, the targeted therapy includes the use of gefitinib, erlotinib, or a combination thereof.

In certain embodiments of the present invention, the method further includes administering at least one additional diagnostic test to the subject to diagnose lung cancer in the subject. In certain embodiments of the present invention, the at least one additional diagnostic test is a blood count test, a blood chemistry test, a chest x-ray, a computed tomography (CT) scan, a magnetic resonance imaging (MRI) scan, a positron emission tomography (PET) scan, sputum cytology, a needle biopsy, bronchoscopy, mediastinoscopy, mediastinotomy, thoracentesis, thoracoscopy, a bone marrow biopsy, or a combination thereof.

In certain embodiments of the present invention, the method further includes determining the level of isoform 1 of subunit 4 of cytochrome c oxidase (COX4-1) in a sample and comparing the level of COX4-2 to COX4-1, wherein a lower ratio of COX4-1 to COX4-2 indicates the presence of lung cancer in the sample.

Cytochrome c Oxidase (COX)

Cytochrome c oxidase (COX) is the terminal enzyme of the mitochondrial respiratory chain and consumes the vast majority of cellular oxygen. COX is composed of 13 subunits per monomer and functions as a dimer. In addition to the 3 largest mitochondrial encoded subunits, the mammalian enzyme contains 10 nuclear encoded subunits, which are partly expressed in a tissue specific and developmental manner (Grossman et al., 1997). The role of COX as the rate-limiting enzyme of oxidative metabolism has been shown in a variety of human cell types and a mouse cell line with a mutation in COX subunit I (Villani et al., 1998; Acin-Perez et al., 2003).

COX subunit 4 (COX 4) is the largest nuclear encoded subunit and contacts catalytic subunits I and II (Tsukihara et al., 1996). For the cow heart enzyme, the ubiquitously expressed COX subunit isoform 4-1 has been shown to bind ATP on the matrix side, leading to allosteric inhibition of enzyme activity at high intramitochondrial ATP/ADP ratios (Arnold et al., 1999). This switch-like function of COX IV allows enzyme activity to be adjusted to physiological energy demand.

A lung-specific isoform of COX subunit IV (COX4-2) was recently discovered in mammals (Hüttemann et al., 2001). Northern analysis and quantitative PCR with human and rat tissues showed high COX4-2 expression in adult lung and trachea and lower expression in all other tissues investigated, including fetal lung. While not intended to be a limitation of the invention, the downregulation of the COX4-2 gene in lung cancer appears to be an important, possibly essential, step during neoplastic transformation, providing COX with the ubiquitously expressed COX4-1 isoform, which is present in low oxygen tissues; cancer cells, especially in solid tumors, are often oxygen depleted, a condition that together with the expression of the lung isoform might further impair energy production and thus cancer cell survival.

The switching from aerobic to glycolytic metabolism in tumor and transformed cells has been known for decades (Vaupel et al., 1989; Rodriguez-Enriquez and Moreno-Sanchez, 1998). Therefore, a low oxidative metabolism likely represents the physiological status of rapidly proliferating cells similar to embryonic cells (Pedersen, 1978). Indeed, lymphocytes, enterocytes, and fetal tissues are not very oxidative (Cuezva et al., 1997; Sodhi et al., 2001), whereas highly oxidative tissues such as kidney cortex or brain are normally quiescent. Strong evidence is presented herein that COX switches back to the embryonic enzyme version during lung cancer development and in cancerous cells. COX lacking the lung isoform 4-2 appears to be less active, which can be interpreted as an adaptation to a switching from aerobic to glycolytic metabolism. COX subunit 4-2 is a focal point in regulating aerobic versus anaerobic metabolism in the lung and is a functional biomarker.

Thus, in addition to being an excellent lung cancer marker, COX is also a target for therapeutic intervention. Thus, also provided herein are assays and screens useful for identifying agents that increase or decrease the expression of COX, e.g., COX4-1 and/or COX4-2. Agents that increase the expression from, e.g., the COX4-2 gene, will be useful in treating and/or preventing cancer, e.g., lung cancer.

Probe ligation and rolling circle amplification. A novel diagnostic assay is described herein. The assay combines the capabilities of both ligation-based assays and rolling circle amplification (RCA). In ligation-based assays, two recognition sequences anneal to the fragment of interest and then are ligated. When ligated, they are very stable, resisting washing steps that remove non-ligated sequences. Such ligation-based assays are extremely specific, since two independent sequences must bind simultaneously to the correct fragment (Landegren 1993; Landegren et al. 1996). In RCA, a strand displacing polymerase such as Phi 29 replicates a circular template over and over again as it proceeds along the circle under isothermal conditions. As a result, the replicated sequence is multiplied, e.g., 1,000-fold or more. Combining RCA with recognition sequences for fluorophores (e.g., molecular beacons), results in an easily visualized, highly amplified signal. The combination of ligation with RCA is attractive. However, the laboratories that work with RCA have reported difficulties. For example, difficulties have been reported amplifying padlock probes that remain catenated to their target (Christian et al. 2001). It has also been reported that so long as the probe remains catenated to the target sequence, replication of the probe does not occur (Baner et al. 1998). Approaches to overcome steric hindrance include shortening or digesting the target sequences completely by exonucleases before amplification. However, in that case, the RCA products would no longer be tethered to the target, as is required for an in situ assay. Certain embodiments of the present invention combine the use of oligonucleotide stems that are attached to target recognition sequences and that also anneal to preformed circles with ligation-based hybridization. It is a technique that preserves the proven advantages of the specificity of ligation-based assays and the amplification power of RCA while spatially separating them so that they can each work effectively.

The Lungs and Lung Cancer

The lungs are two sponge-like organs. Air goes into the lungs through the trachea. The trachea divides into tubes called the bronchi, which divide into smaller branches called the bronchioles. At the end of the bronchioles are tiny air sacs known as alveoli. Many tiny blood vessels run through the alveoli, absorbing oxygen from the inhaled air into the bloodstream and releasing carbon dioxide. Taking in oxygen and getting rid of carbon dioxide are the lungs' main function. A slippery lining, called the pleura, surrounds the lungs. This lining protects the lungs and helps them slide back and forth as they expand and contract during breathing.

Most lung cancers start in the lining of the bronchi. That is why another term for lung cancer is bronchogenic cancer. Lung cancer can also form in glands below the lining of the bronchi, frequently in the periphery of the lungs. Lung cancers are thought to develop over a period of many years. First, there may be areas of precancerous changes in the lung. These precancerous changes often progress to true cancer. It would be very useful to be able to detect these precancerous changes. As a cancer develops, the cancer cells may produce chemicals that cause new blood vessels to form nearby. These new blood vessels nourish the cancer cells, which can continue to grow and form a tumor large enough to see on x-rays. Cells from the cancer can break away from the original tumor and spread to other parts of the body. This process is called metastasis.

There are two major types of lung cancer: small cell lung cancer (SCLC) and non-small cell lung cancer (NSCLC). If a lung cancer has characteristics of both types it is called a mixed small cell/large cell carcinoma.

About 13% of all lung cancers are the small cell type (SCLC), named for the small round cells that make up these cancers. SCLC tends to spread widely through the body. The cancer cells can multiply quickly, form large tumors, and spread to lymph nodes and other organs such as the bones, brain, adrenal glands, and liver. This type of cancer often starts in the bronchi near the center of the chest. Small cell lung cancer is almost always caused by smoking. It is very rare for someone who has never smoked to have small cell lung cancer. Other names for SCLC are oat cell carcinoma and small cell undifferentiated carcinoma.

The remaining 87% of lung cancers are non-small cell (NSCLC). There are three sub-types of NSCLC. The cells in these sub-types differ in size, shape, and chemical make-up. About 25%-30% of all lung cancers are squamous cell carcinomas. They are associated with a history of smoking and tend to be found centrally, near a bronchus. Adenocarcinomas account for about 40% of lung cancers. Adenocarcinoma is usually found in the outer region of lung. People with one type of adenocarcinoma, known as bronchioloalveolar carcinoma (sometimes called bronchoalveolar carcinoma or bronchioalveolar carcinoma) tend to have a better prognosis than those with other types of lung cancer. Large-cell undifferentiated carcinomas are a type of cancer that accounts for about 10%-15% of lung cancers. It may appear in any part of the lung, and it tends to grow and spread quickly resulting in a poor prognosis.

In addition to the 2 main types of lung cancer, other tumors can occur in the lungs. Some of these are non-cancerous (benign). Carcinoid tumors of the lung account for fewer than 5% of lung tumors. Most are slow-growing tumors that are called typical carcinoid tumors. They are generally cured by surgery. Although some typical carcinoid tumors can spread, they usually have a better prognosis than small cell or non-small cell lung cancer. Cancers intermediate between the benign carcinoids and small cell lung cancer are known as atypical carcinoid tumors.

Lung Cancer Stages

Staging is the process of determining how localized or widespread cancer is. It describes how far the cancer has spread. The treatment and prognosis depend, to a large extent, on the cancer's stage. Tests such as CT, MRI, scans, bone marrow biopsy, mediastinoscopy, and blood tests are used to stage the cancer.

Staging of Non-Small Cell Lung Cancer

The system used to describe the growth and spread of non-small cell lung cancer (NSCLC) is the TNM staging system, also known as the American Joint Committee on Cancer (AJCC) system. T stands for tumor (its size and how far it has spread within the lung and to nearby organs), N stands for spread to lymph nodes, and M is for metastasis (spread to distant organs). In TNM staging, information about the tumor, lymph nodes, and metastasis is combined and a stage is assigned to specific TNM groupings. The grouped stages are described using the number 0 and Roman numerals from I to IV (1 to 4). Some stages are subdivided into A and B.

In some cancers, another measure called grade is used. This reflects the pathologist's assessment of how fast the cancer is growing and how likely it is to spread. This is not usually done for lung cancer.

Non-Small Cell Lung Cancer T Stages

Tis: Cancer is found only in the layer of cells lining the air passages. It has not invaded other lung tissues. This stage is also known as carcinoma in situ.

T1: The cancer is no larger than 3 centimeters (slightly less than 1¼ inches), has not spread to the membranes that surround the lungs (visceral pleura), and does not affect the main branches of the bronchi.

T2: The cancer has one or more of the following features: it is larger than 3 cm; it involves a main bronchus, but is not closer than 2 cm (about ¾ inch) to the point where the trachea (windpipe) branches into the left and right main bronchi (carina); it has spread to the membranes that surround the lungs (pleura). The cancer may partially clog the airways, but this has not caused the entire lung to collapse or develop pneumonia.

T3: The cancer has one or more of the following features: spread to the chest wall, the breathing muscle that separates the chest from the abdomen (diaphragm), the membranes surrounding the space between the two lungs (mediastinal pleura), or membranes of the sac surrounding the heart (parietal pericardium); invades a main bronchus and is closer than 2 cm (about ¾ inch) to the point where the windpipe (trachea) branches into the left and right main bronchi, but does not affect this area; has grown into the airways enough to cause an entire lung to collapse or to cause pneumonia in the entire lung.

T4: The cancer has one or more of the following features: spread to the space behind the chest bone and in front of the heart (mediastinum) the heart, the where the windpipe branches into the left and right main bronchi; two or more separate tumor nodules are present in the same lobe, windpipe (trachea), the esophagus (tube connecting the throat to the stomach), the backbone, or the point; there is a fluid containing cancer cells in the space surrounding the lung.

Non-Small Cell Lung Cancer N Stages

N0: No spread to lymph nodes.

N1: Spread to lymph nodes within the lung and/or located around the area where the bronchus enters the lung (hilar lymph nodes). Metastases affect lymph nodes only on the same side as the cancerous lung.

N2: Spread to lymph nodes around the point where the windpipe branches into the left and right bronchi or in the space behind the chest bone and in front of the heart (mediastinum). Affected lymph nodes are on the same side of the cancerous lung.

N3: Spread to lymph nodes near the collarbone on either side, to hilar or mediastinal lymph nodes on the side opposite the cancerous lung.

Non-Small Cell Lung Cancer M Stages

M0: No spread to distant organs or areas. Sites considered distant include other lobes of the lungs, lymph nodes further than those mentioned in N stages, and other organs or tissues such as the liver, bones, or brain.

M1: The cancer has spread distantly.

Stage Grouping for Non-Small Cell Lung Cancer

Once the T, N, and M categories have been assigned, this information is combined (stage grouping) to assign an overall stage of 0, I, II, III, or IV. Patients with lower stage numbers have a better prognosis.

Stage 0; Tis, N0, M0: The cancer is found only in the layer of cells lining the air passages. It has not invaded other lung tissues nor spread to lymph nodes or distant sites.

Stage IA; T1, N0, M0: The cancer is no larger than 3 centimeters, has not spread to the membranes that surround the lungs, does not affect the main branches of the bronchi and has not spread to lymph nodes or distant sites.

Stage IB; T2, N0, M0: The cancer is larger than 3 cm, or involves a main bronchus, but is not near the carina or it has spread to the pleura or the cancer is partially clogging the airways. It has not spread to lymph nodes or distant sites.

Stage IIA; T1, N1, M0: The cancer is no larger than 3 centimeters, has not spread to the membranes that surround the lungs, does not affect the main branches of the bronchi. It has spread to nearby or hilar lymph nodes, but not to distant sites.

Stage IIB; T2, N1, M0 or T3, N0, M0: The cancer is larger than 3 cm, or involves a main bronchus, but is not near the carina or it has spread to the pleura or the cancer is partially clogging the airways. It has spread to nearby or hilar lymph nodes, but not to distant sites, OR, It has spread to the chest wall or the diaphragm, the mediastinal pleura, or membranes surrounding the heart, or it invades a main bronchus and is close to the carina or it has grown into the airways enough to cause an entire lung to collapse or to cause pneumonia in the entire lung. It has not spread to lymph nodes or distant sites.

Stage IIIA; T1 or 2, N2, M0 or T3, N1 or 2, M0: The cancer can be any size, or involves a main bronchus, but is not near the carina or it has spread to the pleura or the cancer is partially clogging the airways. It has spread to nodes in the middle of the chest (mediastinum), but not to distant sites, OR, It has spread to the chest wall or the diaphragm, the mediastinal pleura, or membranes surrounding the heart, or it invades a main bronchus and is close to the carina or it has grown into the airways enough to cause an entire lung to collapse or to cause pneumonia in the entire lung. It has spread to lymph nodes anywhere in the chest on the same side as the cancer, but not to distant sites.

Stage IIIB; T1, 2 or 3, N3, M0 or T4, N0, 1, 2 or 3, M0: The cancer can be of any size. It has spread to lymph nodes around the collarbone on either side, or to hilar or mediastinal lymph nodes on the side opposite the cancerous lung OR, It has spread to the mediastinum, the heart, the windpipe (trachea), the esophagus (tube connecting the throat to the stomach), the backbone, or the carina or two or more separate tumor nodules are present in the same lobe, or there is a fluid containing cancer cells in the space surrounding the lung. The cancer may or may not have spread to lymph nodes. It has not spread to distant sites.

Stage IV; Any T, Any N, M1: The cancer has spread to distant sites.

Staging of Small Cell Lung Cancer

Although small cell lung cancers can be staged like NSCLC, most doctors prefer a 2-stage system. These are "limited stage" and "extensive stage." Limited stage usually means that the cancer is only in one lung and in lymph nodes on the same side of the chest.

Spread of the cancer to the other lung, to lymph nodes on the other side of the chest, or to distant organs indicates extensive disease. Many doctors consider small cell lung cancer that has spread to the fluid around the lung an extensive stage.

Small cell lung cancer is staged in this way because it helps separate patients who have a fair prognosis and may be cured, from those who have a worse outlook with no chance of cure. About two-thirds of the people with small cell lung cancer have extensive disease when their cancer is first found.

Thus, certain embodiments of the present invention are directed to methods for detecting lung cancer at the earliest stage possible, e.g., at or before any of the stages of presentation of lung cancer, such as those listed herein.

Certain embodiments of the invention will now be illustrated by the following non-limiting Example(s).

Example 1

COX4-2 is Highly Expressed in Lung and Trachea

Figure 2:
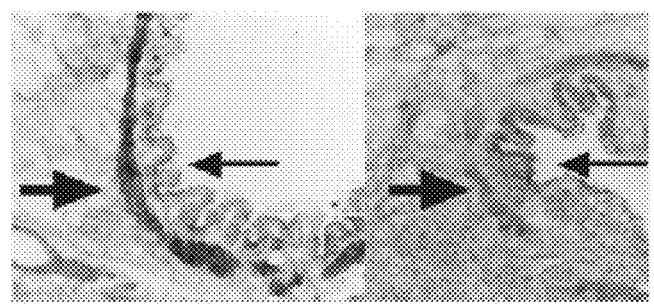
FIG. 2. In situ hybridization of cytochrome c oxidase subunit isoforms 4-1 (right) and 4-2 (left) in rat lung tissue.

The COX4-2 isoform is highly expressed in lung and trachea, where it constitutes about half the subunit 4 transcript, as determined by quantitative PCR (FIG. 1). To localize the site where COX4-2 is synthesized, in situ hybridization was performed with lung samples. These showed that message was found in smooth muscle, in addition to other lung cell types such as epithelia and fibroblasts (FIG. 2). By contrast, COX4-1 staining was strongest in the lining respiratory epithelium.

FIG. 1 depicts the relative quantitative PCR of cytochrome c oxidase subunit isoforms 4-1 and 4-2. Experiments were performed as described (Hüttemann et al., 2001). %[COX4-1]+%[COX4-2]=100%. Relative amounts of COX4-2 transcripts are indicated.

FIG. 2 depicts in situ hybridization of cytochrome c oxidase subunit isoforms 4-1 (right) and 4-2 (left) in rat lung tissue. Shown is a large bronchiole with surrounding tissue. Strong staining was detected for the 4-1 isoform in the respiratory epithelium (smaller arrow, right), whereas a stronger signal was observed for COX4-2 in smooth muscle (larger arrow, left). A control incubated with the labelled sense RNAs of both isoforms showed no staining (not shown). In situ hybridizations were carried out with a DIG-labelled antisense RNA followed by an alkaline phosphatase reaction utilizing BM-purple dye (Roche).

Example 2

COX4-2 is Downregulated in Lung Cancer

A quantitative TaqMan real time PCR was used to investigate the changes in gene expression levels of both isoforms in six lung cancers. Fluorescent probes and primers for both COX subunit 4 isoforms were used. RNA isolation and TaqMan PCR were performed.

The quantitative PCR approach is based on the comparison of both isoform transcript levels in lung cancer and normal lung tissue. COX4-1, the ubiquitously expressed homologue to the lung gene COX4-2, can serve as an internal standard. COX4-1 shows no significant changes in cancer compared to control tissue, as shown by in situ hybridization. COX4-1 can serve as a standard with respect to COX4-2, both 1) externally, because its expression levels are similar under a variety of conditions, and 2) internally, because it is part of the same enzyme, providing a solid basis for expression changes of COX4-2.

Figure 3:
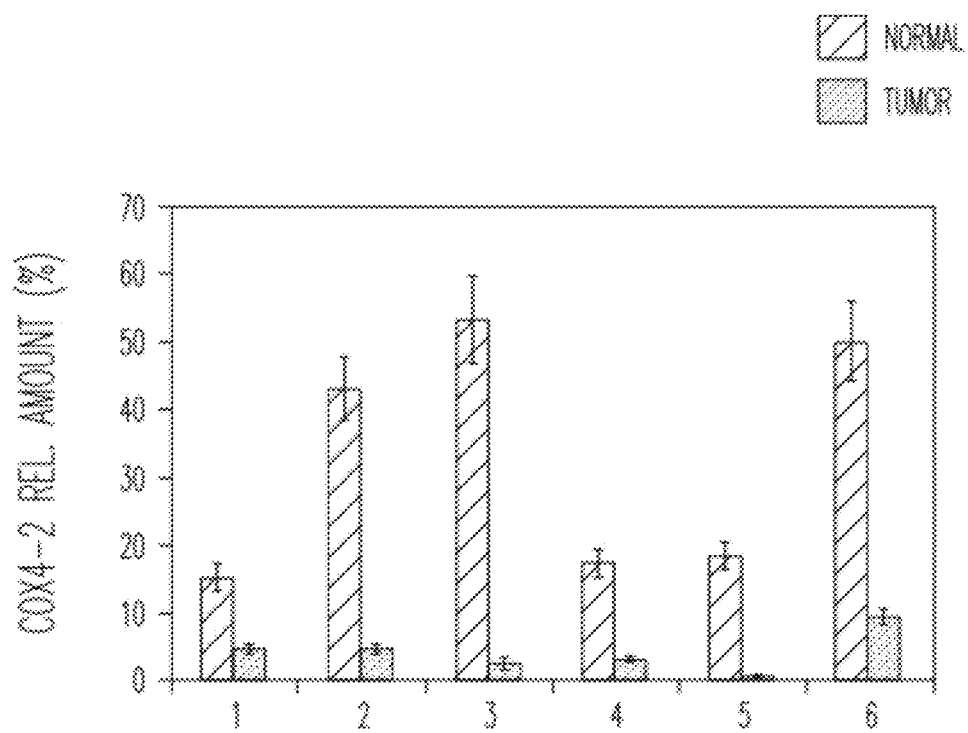
FIG. 3. Quantitative TaqMan PCR shows significant decrease of COX4-2 transcripts in the cancers of all 6 patients.
Figure 4:
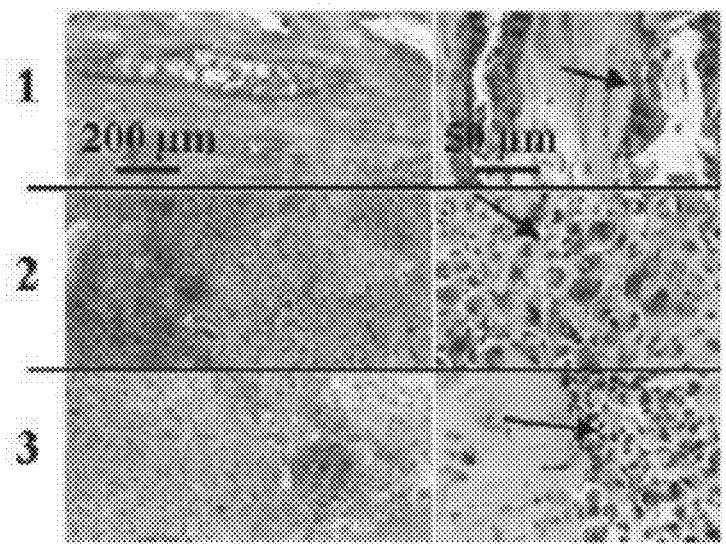
FIG. 4. Hematoxylin-Eosin (HE) stained sections. (1). A lung adenocarcinoma, showing malignant glands (arrow), surrounded by stroma, (2). A squamous cell carcinoma, composed of sheets of large polygonal cells with eosinophilic cytoplasm (arrow). (3). A mesothelioma.

Data obtained are striking in that they show a highly significant decrease in COX4-2 expression in all cancer samples including three adenocarcinomas, two squamous cell carcinomas, and a mesothelioma sample (FIG. 3). These changes were observed even though the cancer samples contained in part normal cells (see FIG. 4). The "normal" samples as defined by routine pathology of patients 1, 4, and 5 contain COX4-2 levels significantly lower compared to "normal" patient samples 2, 3, and 6. According to the hypothesis that downregulation of COX4-2 is an early process during carcinogenesis, the "normal" tissue analyzed likely contains neoplastic lesions that are undetectable using routine pathology but are easily detectable with the COX4-2/COX4-1 marker system. An analysis of stage I lung cancers revealed that COX4-2 transcription is dramatically downregulated (Table 1).

TABLE 1

COX4-2 transcript levels in four stage I lung cancer samples.

| Stage 1 lung cancers | % COX4-2 |
| --- | --- |
| Squamous cell carcinoma | 4.0 |
| Squamous cell carcinoma | 1.4 |
| Adenocarcinoma | 0.7 |
| Adenocarcinoma | 6.5 |

FIG. 3 depicts quantitative TaqMan PCR results and shows a significant decrease of COX4-2 transcripts in the cancers of all 6 patients. Matching normal lung tissue (blue) and lung cancer tissue (red) of six patients were analyzed. COX4-2 transcript levels were normalized to COX4-1 levels. Adenocarcinomas, patient 1, 5, and 6; squamous cell carcinomas, patients 2 and 4; mesothelioma, patient 5.

Example 3

COX4-2 is Downregulated at Early Lung Cancer Stages

RNA samples from SV-40 immortalized but non-transforming bronchial epithelial Beas2-B cells were examined. These cells were treated with 5 µg/mL Cigarette Smoke Condensate (CSC) in DMSO to induce malignant transformation as determined by colony forming efficiency analyzed after each passage (Siddiq et al., 2004). Significant changes were observed only after passage 18 in the presence of CSC, with a more than 4 fold increase in colony forming efficiency (Siddiq et al., 2004). COX4-2 transcript levels were tested via TaqMan PCR at passage 18, but also at the earliest passage available, passage 9. Four clones were also included that were expanded from soft agar after passage 18 and CSC treatment because malignant transformation efficiency is further increased 2-3 fold (Siddiq et al., 2004). In addition, other established lung cancer cell lines were also included. Again, the data were striking in that COX4-2 transcript levels were near background level in all samples, a more than 10,000 fold downregulation, including, notably, the early passages that macroscopically are non-transforming (Table 2). Thus, COX4-2 transcription is decreased in the cancer cells, and the decrease occurs at very early stages during transformation.

TABLE 2

COX4-2 transcript levels in cell lines treated with or without Cigarette Smoke Condensate (CSC). Normal lung epithelial cell line Beas2-B was grown for different time periods (passages 9 and 18) and treated with CSC in DMSO and DMSO alone as control. Other cell lines were included for comparison (HTB182, 5800, 5810, 5298, H460).

| Cell line | % COX4-2 |
| --- | --- |
| Beas2B DMSO P9 | not detectable |
| Beas2B CSC P9 | <0.002 |
| Beas2B P9 | <0.004 |
| Beas2B P18 | not detectable |
| Beas2B DMSO P18 | not detectable |
| Beas2B CSC P18 | not detectable |
| HTB 182 | <0.002 |
| 5800 | <0.003 |
| 5810 | <0.004 |
| 5298 | <0.001 |
| H460 | not detectable |
| Beas2B Clone 1 | not detectable |
| Beas2B Clone 2 | <0.003 |
| Beas2B Clone 3 | <0.009 |
| Beas2B Clone 4 | <0.003 |

Example 4

COX4-2 is an Early Lung Cancer Biomarker

The differential expression of the two isoforms of COX4 affords an ideal biomarker to be used in an assay for early detection of lung cancer because it involves an isoform specific to lung tissue that is downregulated in lung cancer at an early stage, and the standard against which its downregulation is measured is highly but constantly expressed and is itself the alternate isoform of the same subunit. However, the use of the COX4 early marker system and the diagnostic assay development do not depend on each other. In the case that COX4-2 is downregulated in less than the vast majority of lung cancer samples, the proposed assay can still be used with other marker gene(s).

(a) COX4-2/COX4-1 Transcript Levels in Lung Cancers.

That COX4-2 is a lung cancer marker has been verified on a larger number of lung cancer samples and from matching controls. TaqMan real time PCR was used with primers and fluorescent probes ("MGB"-probes, Applied Biosystems) for COX4-2 and COX4-1. RNA was obtained from tumor samples immediately frozen after surgery and controls (ca. 150-300 mg each sample). Control lung tissue samples were obtained from the marginal regions of the tissue. All samples that were used were derived from waste tissue after lung surgery. In addition, lung samples from individuals with no lung disease, in particular no lung cancer history, were used as additional controls. Sample include, e.g., stage 1 lung cancer samples and matching controls. COX4-2 downregulation can be found in all cancer samples.

Statistical method: Quantitative RT-PCR data was statistically analyzed.

b) A Diagnostic Test for the Early Detection of Lung Cancer

It is expected that neoplastic cells will be outnumbered by normal cells and thus standard assays such as quantitative PCR or ELISA based on cell mixtures may not be optimal for early detection; the earlier the neoplastic lesion, presumably the more diluted are the malignant cells among normal cells.

Thus, an assay based on individual cells is proposed herein. In certain embodiments, cells that only produce signals for the COX4-1 isoform will indicate the presence of neoplasia.

Figure 5A:
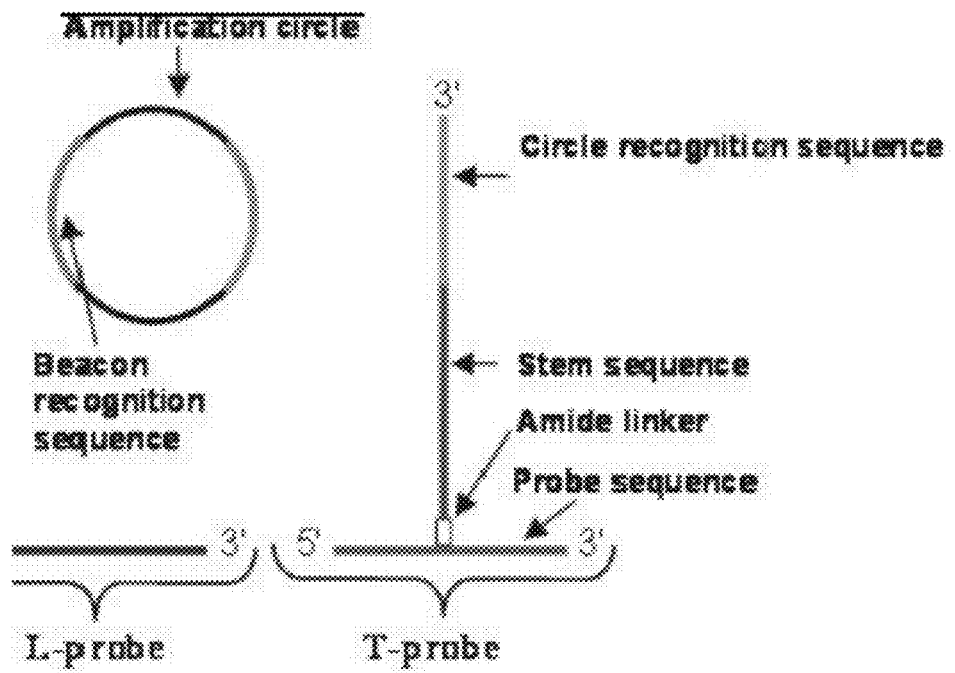
FIG. 5A-C. A schematic representation of an assay of one embodiment of the invention.

Experimental design: An assay based on the differential expression of the two isoforms, a reliable in situ technique that can distinguish between cells expressing normal amounts of COX4-2, and those cells expressing markedly lower amounts or no COX4-2, is described herein. The technique is a modification of rolling circle amplification (RCA). One circular probe can be used for each of the two genes whose expression is to be detected (COX4-1 and COX4-2 in this case), with molecular beacon recognition sequences that will distinguish the two visually (amplification circle, FIG. 5A).

An advantage of using a stem-based RCA approach is to circumvent steric hindrance of the polymerase during amplification that is usually observed in standard RCA. However, specificity can be lost if only one gene-specific probe is used. In addition, robustness of the assay may sometimes be problematic because washing conditions, such as salt concentration and temperature, may have to be precisely controlled: if washing occurs under too stringent conditions the stem probe can be pulled off the target mRNA, leading to false negative results.

In order to combine robust stem-based amplification with specificity, two probes for each COX4 mRNA (L- and T-probe, FIG. 5A) have been designed. Both probes anneal to adjacent regions on the target mRNA to allow subsequent amplification after they have been ligated, e.g., using T4 DNA ligase. Washing conditions can be chosen in a broad temperature window due to an about 15° C. increase of the calculated melting temperatures of the ligated probes containing the L- and T-sequence, compared to the unligated T-probes. Thus, a washing step will remove any unligated probe, which provides complete specificity, and for the signal to be generated by RCA the two recognition sequences, each unique to the gene of interest, would both have to anneal.

Figure 5B:
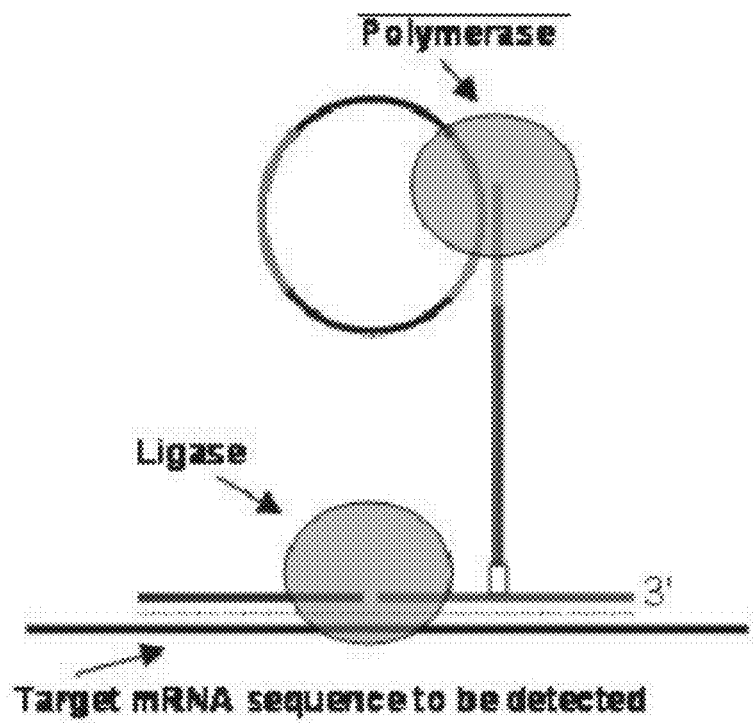
Figure 5C:
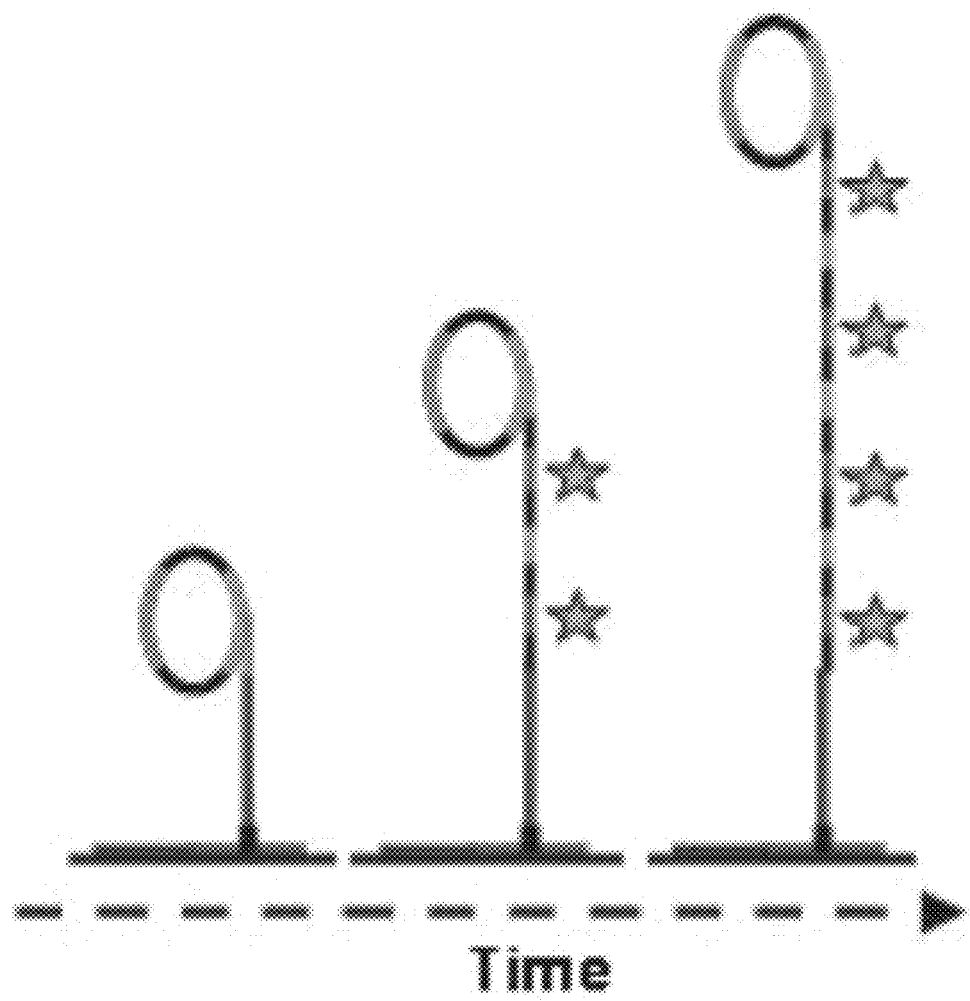

FIG. 5 depicts a schematic representation of an assay of the invention. As depicted in 5A, the assay involves the use an amplification circle, a T-shaped probe (T-probe), and a second probe (L-probe) to be ligated to the T-probe. As depicted in 5B, after cells have been fixed on slides, the probes are added and anneal to their target mRNA. A ligase concatenates both probes, which leads to an increased Tm for the ligated probe. Applying stringency washes, T- or L-probes that are not ligated are removed whereas the ligated probe remains bound. The single stranded amplification circle is added, which anneals to the circle recognition sequence of the T-probe, which serves as a primer for RCA. As depicted in 5C, the strand replacement polymerase extends the circle recognition sequence going around the circle many times (RCA), generating many copies of the Beacon recognition sequence for subsequent fluorescent detection (green star). This approach spatially separates the RCA reaction from the target sequence, eliminating steric hindrance of standard RCA, but still maintaining high specificity due to the requirement of the L- and T-probe ligation. The reaction can be multiplexed using different circle recognition sequences and amplification circles for the respective biomarker(s).

The probes (see Table 3) contain several features: (1) they span exon-exon junctions, preventing amplification of genomic DNA; (2) their sequences are unique with respect to the human genome and EST database; (3) the probes have similar melting temperatures, allowing washing steps under similar stringency when multiplexed; (4) the T-probe is 5'-phosphorylated to allow ligation to the L-probe; (5) the T-probes contain either a 3-carbon spacer or a di-deoxy cytosine at the 3'-end to prevent 3'-amplification of the probe, important because unspecific annealing of the T-probe to any other mRNA template could otherwise lead to the 3'-extension of the probe during the amplification phase, which would increase the melting temperature of the T-probe with its unspecific target, preventing controlled removal of misannealed probes during subsequent washing steps; and (6) the T-probe contains an amino group attached by a 6-carbon linker to a thymine nucleotide in the middle of the probe, which allows efficient synthesis of the full T-probe containing the stem part via specific coupling chemistry (see below). The position of the modified thymine nucleotide within the sequence was designed to provide enough space for the footprint of the relatively small T4 ligase on the 5'-phosphate side of the ligation to link the L- and T-probes (Ng et al., 2004, found that T4 ligase requires 6 bp on the 5'-phosphate side of the nick for efficient ligation).

TABLE 3

Specific probes for COX4-1/COX4-2 detection.
The T-probes contain a 5'-phosphate (P), and
$C_6$-amino modified T base (*), and a 3'-spacer
(spC3) or a dideoxy 3' base (ddC).

|  | L-probe | T-probe |
| --- | --- | --- |
| COX4-1 | 5'-<br>TACGAGCTCATGAAAGTG<br>TTGTGAAGAGC-3'<br>(SEQ ID NO: 1) | 5'-P-<br>GAAGACTTTT*CGCTCCCAGs<br>pC3-3'<br>(SEQ ID NO: 2) |
| COX4-2 | 5'-<br>TTGGTGGCAGCGGGTCT<br>ACGTATTTCCTC-3'<br>(SEQ ID NO: 3) | 5'-P-<br>CAAAGCCGAT*CACCTTGAdd<br>C-3'<br>(SEQ ID NO: 4) |

Coupling reaction: To generate the T-probe, which includes the sequence complementary to the target mRNA and the stem for initiating RCA, any method available to the art may be employed. For example, diimide coupling chemistry can be utilized, which specifically links a carboxyl with an amine moiety, generating an amide bond: in the presence of the water-soluble compound EDC (1-ethyl-3-[3-dimethylaminopropyl]carbodiimide hydrochloride) the amide bond is specifically formed, preventing the formation of by-products as observed when using mono-functional coupling reactions (see Reaction 1). The coupling reaction products will be analyzed by mass spectrometry.

Reaction 1

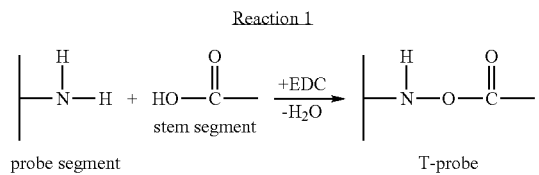

Figure 6:
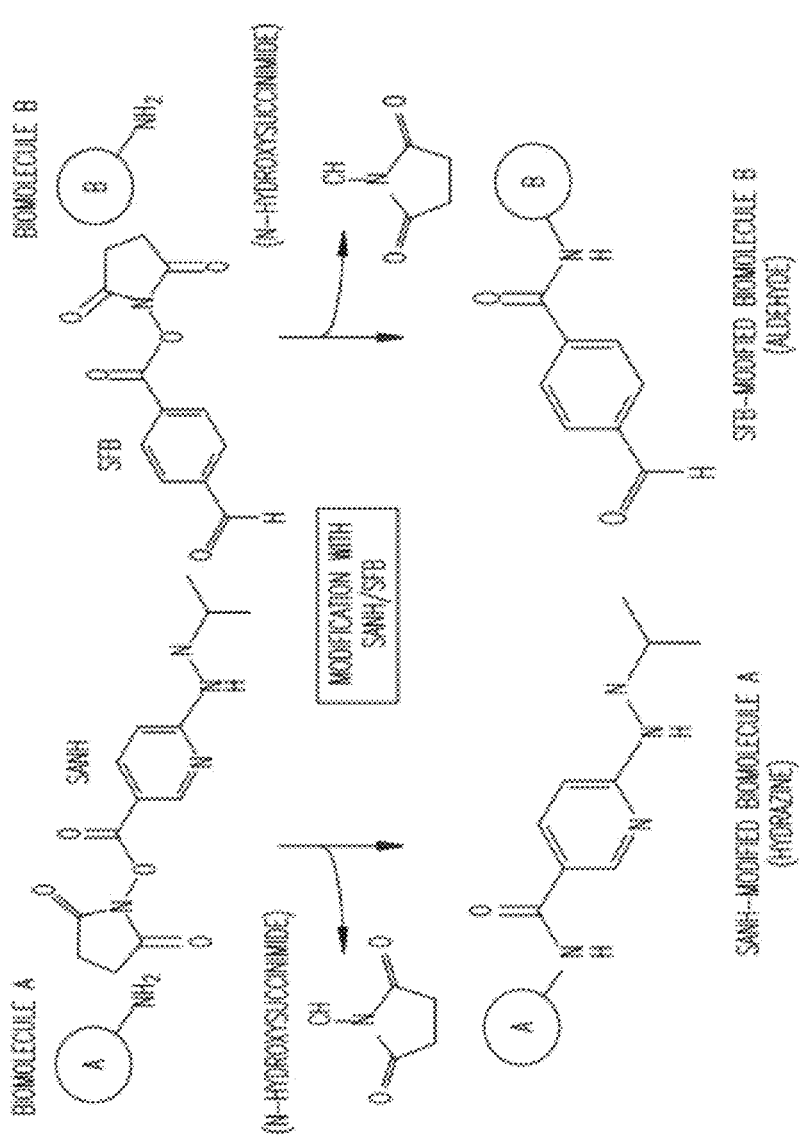
FIG. 6. The chemical modification of two biomolecules using SANH and SFB heterobifunctional Linkers.
Figure 7:
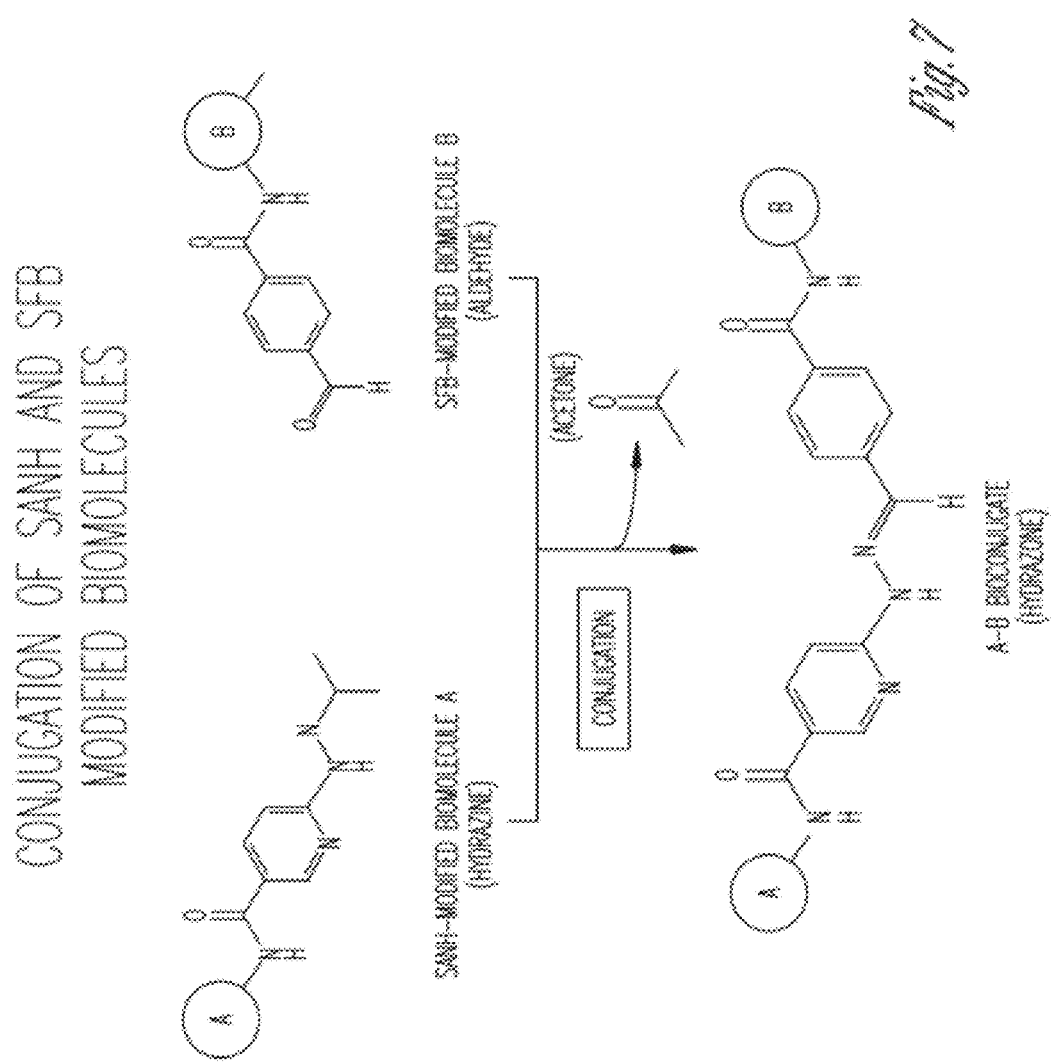
FIG. 7. Conjugation of SANH and SFB Modified Biomolecules.

Another method of generating the T-probe is through the use of SANH and SFB linkers (FIGS. 6 and 7; KPL, Inc., Gaithersburg, Md.). SANH (Succinimidyl 6-hydrazinonicotinamide acetone hydrazone) and SFB (Succinimidyl 4-formylbenzoate) are heterobifunctional crosslinkers that can be used to modify amine-containing biomolecules or surfaces. SANH and SFB can individually modify biomolecules in preparation for conjugation. SANH and SFB will modify biomolecules by incorporating hydrazine and benzaldehyde moieties, respectively. The protecting group on SANH hydrolyzes in acidic or neutral pH (4.5-7.4) and the liberated hydrazine moiety reacts with the aldehyde modified biomolecules to produce hydrazone conjugates (see below). Biomolecules modified with either SANH and SFB are stable for long periods of time, e.g., months.

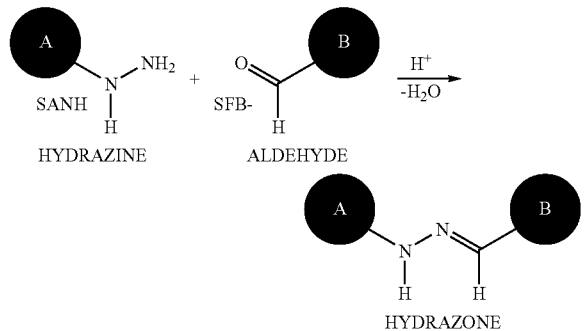

In essence, reactive group may be placed internally in a probe. As used herein, "reactive group" includes a moiety on the compound that is capable of chemically reacting with a functional group on a different compound to form a covalent linkage. Typically the reactive group is an electrophile or nucleophile that can form a covalent linkage through exposure to the corresponding functional group that is a nucleophile or electrophile, respectively. Selected examples of reactive groups and linkages are shown in Table 4, where the reaction of an electrophilic group and a nucleophilic group yields a covalent linkage.

TABLE 4

Examples of some routes to useful covalent linkages

| Electrophilic Group | Nucleophilic Group | Resulting Covalent Linkage |
| --- | --- | --- |
| activated esters* | amines/anilines | carboxamides |
| acrylamides | thiols | thioethers |
| acyl azides** | amines/anilines | carboxamides |
| acyl halides | amines/anilines | carboxamides |
| acyl halides | alcohols/phenols | esters |
| acyl nitriles | alcohols/phenols | esters |
| acyl nitriles | amines/anilines | carboxamides |
| aldehydes | amines/anilines | imines |
| aldehydes or ketones | hydrazines | hydrazones |
| aldehydes or ketones | hydroxylamines | oximes |
| alkyl halides | amines/anilines | alkyl amines |
| alkyl halides | carboxylic acids | esters |
| alkyl halides | thiols | thioethers |
| alkyl halides | alcohols/phenols | ethers |
| alkyl sulfonates | thiols | thioethers |
| alkyl sulfonates | carboxylic acids | esters |
| alkyl sulfonates | alcohols/phenols | ethers |
| anhydrides | alcohols/phenols | esters |
| anhydrides | amines/anilines | carboxamides |
| aryl halides | thiols | thiophenols |
| aryl halides | amines | aryl amines |
| aziridines | thiols | thioethers |
| boronates | glycols | boronate esters |
| carbodiimides | carboxylic acids | N-acylureas or anhydrides |
| diazoalkanes | carboxylic acids | esters |
| epoxides | thiols | thioethers |
| haloacetamides | thiols | thioethers |
| haloplatinate | amino | platinum complex |
| haloplatinate | heterocycle | platinum complex |
| haloplatinate | thiol | platinum complex |
| halotriazines | amines/anilines | aminotriazines |
| halotriazines | alcohols/phenols | triazinyl ethers |
| imido esters | amines/anilines | amidines |
| isocyanates | amines/anilines | ureas |
| isocyanates | alcohols/phenols | urethanes |
| isothiocyanates | amines/anilines | thioureas |

TABLE 4-continued

Examples of some routes to useful covalent linkages

| Electrophilic Group | Nucleophilic Group | Resulting Covalent Linkage |
| --- | --- | --- |
| maleimides | thiols | thioethers |
| phosphoramidites | alcohols | phosphite esters |
| silyl halides | alcohols | silyl ethers |
| sulfonate esters | amines/anilines | alkyl amines |
| sulfonate esters | thiols | thioethers |
| sulfonate esters | carboxylic acids | esters |
| sulfonate esters | alcohols | ethers |
| sulfonyl halides | amines/anilines | sulfonamides |
| sulfonyl halides | phenols/alcohols | sulfonate esters |

*Activated esters, as understood in the art, generally have the formula —COΩ, where Ω is a good leaving group (e.g. succinimidyloxy (—OC$_4$H$_4$N$_3$);
sulfosuccinimidyloxy (—OC$_4$H$_3$O$_2$SO$_3$H), -1-oxybenzotriazolyl (—OC$_6$H$_4$N$_3$); or an aryloxy group or aryloxy substituted one or more times
by electron withdrawing substituents such as nitro, fluoro, chloro, cyano, or trifluoromethyl, or combinations thereof, used to form activated aryl esters; or a carboxylic acid activated by
a carbodiimide to form an anhydride or mixed anhydride —OCOR$^a$ or —OCNR$^a$NHR$^b$, where R$^a$ and R$^b$, which may be the same or different, are C$_1$-C$_6$ alkyl, C$_1$-C$_6$ perfluoroalkyl, or C$_1$-C$_8$ alkoxy;
or cyclohexyl, 3-dimethylaminopropyl, or N-morpholinoethyl).
**Acyl azides can also rearrange to isocyanates Assay performance. Cells can be fixed on a slide. During this process membrane holes are generated, allowing enzymes, probes, and other components to enter the cells. L- and T-probes of both COX4 isoforms are annealed to their target RNAs and only ligated if annealed immediately adjacent on the same mRNA strand. Unligated probes can be removed by a washing step at elevated temperature followed by the addition of amplification circles, which anneal to the stem part of T-probe. Extension of the circles can be performed using Phi 29 polymerase for 1 hr at 30° C., and terminated by a washing step. Beacon probes specific for either isoform amplification product can be annealed. A washing step can remove unincorporated beacon probes and the cells can be visualized with a two channel fluorescent microscope.

The assay may be modified by the art worker, starting from the following conditions:

(1) Fixation of cells. The cells can be suspended in SSC. 200 μL can be placed on slides cleaned with ethanol. The slides can then be placed in a cytocentrifuge (700 rpm for 4 min). The slides with fixed cells can be then bathed in methanol to perforate the cells while leaving them and their contents in place. The methanol can be evaporated to dry the cells.

(2) Annealing and ligation of the probes. Annealing and ligation can be performed in ligation buffer (30 mM Tris-HCl (pH 7.8), 10 mM MgCl$_2$, 10 mM DTT and 1 mM ATP) containing 1 μM T-probe, 1 μM L-probe, 3 μM preformed circles, and 20 units T4 DNA ligase (Promega). Appropriate control mixtures can also be made, in which circles, ligase, T-probes, and L-probes are in turn missing from the mixture. The solution can be applied to the slides and held in place by a gasket and cover (MJ Research). The mixture can be ligated for two hours at room temperature.

(3) Washing. The gaskets and covers can be removed, and the slides can be washed in 2×SSC buffer at 65° C. for 5 min with agitation in order to remove unligated T-probe and unannealed circles. The slides can be then air dried.

(4) RCA. DNA syntheses can be performed in amplification buffer (4 mM Tris-HCl (pH 7.5), 5 mM KCl, 1 mM MgCl$_2$, 0.5 mM (NH$_4$)$_2$SO$_4$, 0.4 mM DTT, and 1 μM dNTPs) in the presence of 20 units Phi 29 polymerase (Epicentre). Twenty-five μL of this solution can be applied to each slide, and a gasket and cover can be applied. Slides can be incubated at 30° C. for 1 hour, washed in 2×SSC for 5 min at room temperature, and then soaked in PBS (pH 8), supplemented with 0.1% Nonidet for 5 min at room temperature, in order to remove the polymerase.

(5) Molecular beacons. The circles can be of two types, each including a recognition sequence for one of two different molecular beacons, one that can incorporate the fluorescent dye Oregon Green and can indicate the presence of COX4-2, and another that will incorporate the fluorescent dye Texas Red and can indicate the presence of COX4-1 (any detectable molecule, including but not limited to a fluorophore, can be used in the assays described herein). These fluorescent dyes show clearly distinguishable emission spectra (542 nm and 615 nm, respectively). The beacon recognition sequences have been designed such that the recognition sequence includes the quencher stem sequence, so that the quencher, when annealed, can be held next to the amplified RCA DNA strand, while the fluorophore's hairpin/stem can be free from the amplified product. This can prevent one beacon's quencher from quenching a neighbouring beacon's fluorophore (Nilsson et al., 2002). The beacons (4 µM) along with annealing buffer (30 mM Tris-HCl (pH 7.8), 10 mM $MgCl_2$, 10 mM DTT) can be added to the RCA reaction products on the slides, and the mixture can be heated to 70° C. to denature the beacons, and then cooled to room temperature to allow them to anneal to the recognition sequences. The slides can then be soaked in SSC at room temperature for 5 min, and then soaked in PBS (pH 8), with 0.1% Nonidet for 5 min at room temperature, to remove unbound beacons to further reduce background signal.

(6) Data analysis. The slides can be visualized using a Nikon E-600 FE fluorescent microscope connected to a Retiga 1300 digital camera and can be analyzed with Simple PCI image capture software (Compix).

Different salt concentrations may be used in the ligation step. The ligation and RCA steps may be combined in order to make the assay simpler. In doing so, the buffer composition may be modified to be compatible with both T4 ligase and Phi 29 polymerase. The amount of molecular beacon used in step (5) can be optimized for maximum signal with minimum background.

Phase I: Two established human H460 derived cell lines, one overexpressing COX4-1 and the other overexpressing COX4-2 can be examined. These cell lines have been generated by cloning the two COX4 isoform cDNAs in the pcDNA-his/myc vector (Invitrogen), which contains the neo cassette. Transfected cells were selected using G418 and clones containing the genomic plasmid insertion were expanded for four weeks in media containing G418. A mouse fibroblast cell line can be used as negative controls (CRL-2017, available from ATCC). The assay can be optimized for each isoform separately. A successful assay can specifically distinguish cells expressing one isoform from cells expressing the other. The next step is the combination (multiplexing) of both assays. The assay can also be tested on human tissue sections derived from normal and lung cancer samples. Although the primary goal is to develop a non-invasive lung cancer test based on sputum, saliva, and BAL samples, the in situ assay is will work similarly well on tissue sections obtained from surgery or biopsies, which can be an additional useful application for the detection of early stages of neoplastic transformation in tissues obtained by more invasive means.

Phase II: Material from lung cancer patients with different types and stages of cancer can be examined. Specimens to be used in these investigations include biological samples such as sputum and BAL samples from individuals screened as high risk for developing lung cancer, including chronic smokers with evidence of chronic obstructive pulmonary disease. Some bronchial biopsies from these patients as well as from patients with established lung cancer can be used. Sputum analysis may be part of these programs, followed by bronchoscopy in positive cases, which are available in addition to control samples. These samples can be matched for clinical pathological parameters, including smoking history, age, and gender. Sputum and snap-frozen tissue specimens can be promptly delivered to the laboratory. Cells can be collected by centrifugation and divided onto three slides (50-70 cells/slide). The first slide can be used for routine cytological evaluation, the second slide can be used for ligation-based RCA, and the third can be stored frozen at −80° C. for follow up studies or the repetition of the assay in ambiguous cases. Tissue samples can be used to (1) generate at least five 12 micron serial frozen tissue sections for H-E and the assay, and (2) 10-40 mg of the remaining tissue can be used for TaqMan PCR.

Data interpretation, sample size, and alternative outcome. Sputum samples from smokers and ex-smokers can be analyzed. The sputum samples may be stored as cell pellets in cryomedia. Analysis can begin on the subset of samples from individuals with known lung cancer and controls. It is expected that the cancer patient-derived samples will show a higher number of cells not expressing COX4-2. Cells that do not show signals for the control (COX4-1) are not be considered. In the population of cells producing signals for COX4-1 the ratio of cells can be determined that show a lower, e.g., absent, signal for COX4-2. The more advanced the cancer lesion, the more abundant will be cells lacking COX4-2 transcripts. The in situ assay regarding COX4-2 in individual cells can produce easily distinguishable data such that the transcripts are present (normal cells) or absent (all cancer stages). However, in case gradually variable COX4-2 levels are observed after normalization to COX4-1 levels, e.g., in the very earliest stages of transformation, the data analysis will be modified accordingly: instead of having the expected two categories, COX4-2 being absent or present, the scale will be expanded to five categories. The assignment of the categories to cancer advancement can be based on results derived from individuals with known lung cancer and control samples.

Statistical method: Data can be analysed with the Wilcoxon rank sum test (in case binary data are obtained, in which cancer cells express no COX4-2) or t-test (if continuous data are obtained, in which case cancer cells would show a gradual decrease in COX4-2 expression as cancer progresses).

The capacity of the assay for multiplexing means that several biomarkers could be identified in one reaction. The assay can be applied to a variety of other biological samples, such as blood, cell smears, and tissue sections.

Example 5

Probe Ligation and Rolling Circle Amplification for In Situ Detection of mRNA Expression Described herein is a method for in situ detection of gene expression on a cell-by-cell basis, combining the advantages of probe ligation and rolling circle amplification. The novel design of the probe separates probe ligation from rolling circle amplification, thus avoiding problems of steric hindrance that have been encountered with padlock probes. A protocol is described, including high-temperature washing steps that ensure specificity of binding. The protocol was tested on its ability to detect CcO4-1 (Cox4-1) and CcO4-2 (Cox4-2), genes encoding a subunit and its isoform of cytochrome c oxidase (CcO; Cox). The method produces an easily-visualized signal, and is specific, giving a signal for its intended target of human cells in culture, while giving no signal for, e.g., Drosophila cells in culture (control).

Described herein is a novel method for detecting mRNA expression in cells (however other forms of RNA and DNA may be detected as well), for example, on cells fixed on a slide (or, for example, in a tissue section). For certain applications, it is desirable to detect expression on a cell-by-cell basis, instead of in an aggregate of cells. In such a case, it is useful to be able to fix the cells to a slide in a monolayer, and then to perform required reactions on the slide itself. Furthermore, in order to detect RNA expression, it is advantageous to employ a technique that is both specific (meaning that there are as few false positives as possible), and sensitive (meaning that even small amounts of detectable expression can be adequately visualized).

With the above requirements in mind, the following provides an example of a protocol in which cells are fixed to slides, reactions are performed on the slides themselves, and expression is detected by a novel probe which avails itself of probe ligation and rolling circle amplification. Probe ligation ensures specificity, while rolling circle amplification ensures sensitivity.

The principle of probe ligation's efficacy is that where two probes must anneal to the target sequence (an accomplishment that enables ligation of the separate probes to each other), the probability of non-specific binding is dramatically reduced. In addition, two probes when ligated together compose one probe sequence that is strongly and specifically annealed to the target, and will resist washing steps that would wash away non-specifically bound probe. In particular, probe ligation is superior to one long probe, since such a probe may bind at many points to a sequence other than the target.

Rolling circle amplification (RCA) has been recommended for various applications. The main virtue of RCA is that it has the capability of replicating a circular sequence many-fold. Nallur et al. (2001) reported an 8,125-fold amplification. When rolling circle amplification and probe ligation are combined (as in target-primed rolling circle amplification using a padlock probe; Nilsson et al. 1994), the strand-displacing polymerase appears not to work sufficiently effectively. The reason for this may be steric hindrance arising between the polymerase and the target of the probe (Baner et al. 1998; Lizardi et al. 1998; Christian et al. 2001). Described herein is the design of probes so that the rolling circle amplification is physically separated from the probe ligation.

To physically separate ligation of the recognition sequences from RCA, a design that employs a T-shape probe was chosen. This shape, not found in natural oligonucleotides, was constructed using attachment chemistry.

To demonstrate the capabilities of the novel design, it was used to detect isoforms of a subunit of cytochrome c oxidase (CcO), CcO4-1 and CcO4-2. The subunit is one of the 13 subunits of monomeric CcO. For information about subunit 4, please refer to Huttemann et al. 2007; Huttemann et al. 2001; and Huttemann 2000.

Materials and Methods

Conjugation

Sequences of DNA were conjugated in order to form a T-shape. The attachment chemistry would achieve four goals: stability of the bond; efficiency of conjugation; specificity of binding; and availability of materials. One attachment chemistry included primary amines attached to the middle of one oligo, and to the 5' end of the other. Such oligos are easily produced by commercial vendors (e.g., Integrated DNA Technologies). A hydrazone bond was created between them, using linkers succinimidyl 4-hydrazinonicotinate acetone hydrazone (SANH) and succinimidyl 4-formylbenzoate (SFB). SANH and SFB carry the NHS moiety, N-hydroxysuccinimidyl ester, which reacts with nucleophiles such as primary amines to form a stable amide bond. The reaction of the resulting oligos containing either hydrazine or aldehyde moieties yields a stable hydrazone bond by eliminating a water molecule. No reducing reagents are required to form a stable hydrazone. The reaction is acid catalyzed with an optimal pH at 4.7. The reaction can occur up to pH 7.2, although with increasing pH the reaction rate becomes slower due to a decrease in the reaction efficiency. The protocol of the reaction is as follows:

1. To PBS buffer (pH 7.2-7.4, 100 mM) (3.2 µl), add DNA recognition oligo modified with amino group on the appropriate residue (32 µl of 1,000 pmole/µl recognition oligo), and C6-SANH dissolved in DMF (2 mg SANH dissolved into 40 µl DMF), then add 5 µl of this solution to the reaction, and 16 µl of DMF.
2. Incubate at room temperature in the dark for at least 2 hours.
3. Purify with NAPS column (collect in 0.2 mL tubes, analyze at A260; use the drops in the first group of tubes that indicate the appropriate optical density).
4. To PBS buffer (pH 7.2-7.4, 100 mM) (3.2 µl), add DNA "stem" oligo modified with amino group (32 µl of 1,000 pmole/µl stem oligo), SFB dissolved in DMF (2 mg SFB dissolved into 40 µl DMF), then added 5 µl of this mixture to the reaction, and 16 µl DMF.
5. Incubate at room temperature in the dark for at least 2 hours.
6. Purify with NAPS column.
7. Dry collected amounts in speedvac to approximately 50 µl each.
8. Mix the C6-SANH-modified oligo and the SFB-modified oligo in an equal amount of MES (pH 4.7, 100 mM).
9. Incubate at room temperature in the dark for 8-16 hours.
10. Purify with NAPS column.
11. Confirm product with electrospray mass spectroscopy.

Oligos:

While any sequence, e.g., any sequence within human Cox4-2 or Cox4-1 transcripts, may be used, by way of example the following are provided:

The sequences of DNA used to make the components of the assay were as follows:

```
Circularizable probe:
                                        (SEQ ID NO: 5)
5'-
/5Phos/CCTGCCCTGCGAATTCGGGTATAGTGAGTTAAA
TTCATAGGAAACACCAAAGATGATATTTGCTCGGATACATATTTAGTGA
CACTATAGCGAGCCGAGC-3';

Oligo-fluorophore:
                                        (SEQ ID NO: 6)
5'-GCTCGGATACATATTTAGTGACACTATA/36-FAM/-3';

Stem:
                                        (SEQ ID NO: 7)
5'-
/5AmMC6/AACTAACCAATCAGTTCGCTTCTCGCTTTTGCAGGGCAGGGC

TCGGCTCG-3';

COX4-1T-seq:
```

```
                                                    (SEQ ID NO: 8)
5'-/5Phos/GAAGACTTT/iAmMC6T/CGCTCCCAG/3SpC3/-3';

COX4-1 ext:
                                                    (SEQ ID NO: 9)
5'-TACGAGCTCATGAAAGTGTTGTGAAGAGC-3';

CcO4-2 T-seq:
                                                    (SEQ ID NO: 10)
5'-/5Phos/CAAAGCCGA/iAmMC6T/CACCTTGA/3ddC/-3';

CcO4-2 ext:
                                                    (SEQ ID NO: 11)
5'-TTGGTGGCAGCGGGTCTACGTATTTCCTC-3'.
```

The COX4-1 T-seq and the COX4-1 ext were made from the cDNA sequence of the COX4-1 human gene, with attention to the inclusion of intron-exon boundaries so that the probe would not anneal to genomic COX4-1 DNA. There is only one genomic sequence that is somewhat similar to the 48-bp ligated probe; in a 48-bp stretch of DNA, 41 of the 48 bases are identical to the probe. The contig within which the sequence is found sequence has NCBI accession numbers NW_001838111.1 and NT_026437.11.

The CcO4-1 and CcO4-2 probes were made so that the two probes were as different as possible from each other, so that they would be able to distinguish CcO4-1 mRNA from CcO4-2 mRNA. The CcO4-1 probe was constructed to follow the sequence of the gene at a place where the homologous CcO4-2 gene has two multi-base deletions and many distinctive bases. The CcO4-2 probe was constructed to follow the sequence of the gene where it is quite distinctive from the CcO4-1 sequence because of many distinctive bases (only 23 of 48 total bases are the same).

Both the CcO4-1 and the CcO4-2 T-seqs begin with a 5' phosphorus, to enable ligation with their respective extensions. They end with a dideoxy cytosine or a three-carbon spacer, each of which prevent elongation from the 3' end.

When the probe hybridizes to the target, and the extension also hybridizes and is ligated, the circularizable probe anneals to the stem, in such a way that the ends of the sequence anneal immediately next to each other, and then are ligated. The stem was attached to the recognition sequence 9 bp from the place where the T-seq and the extension would be ligated, so that there would be enough room for the ligase to bind and perform the ligation reaction. Then the strand-displacing polymerase phi 29 amplifies the circle, using the stem as a primer. The fluor anneals to those (unannealed) parts of the amplified circle that are designed as recognition sequences for the fluor.

Fixation of Cells on Slides.

H460 cells were grown in RPMI medium with 10% fetal bovine serum and 1% penicillin/streptomycin to near-confluence, and trypsinized (TrypLE express, without phenol red, Gibco) to dislodge them from a T-75 flask. 1 mL of the medium with dislodged cells was added to a tube containing 50 mL of the same medium. Then 100 μl of that mixture was pipetted into each of the chambers of a cyto-tek cytocentrifuge (Sakura Finetek, Torrance, Calif.), into which slides were placed along with blotting paper that included a square space in the middle allowing the cells to be spun directly onto the slide, per the manufacturer's instructions. The slides were centrifuged at a speed of 500 rpm for 4 minutes, and the slides were removed and dried.

In the case of the Drosophila cells, the cells were treated as above except that they were trypsinized with TrypLE express diluted three times in 1×PBS, and after two minutes' trypsinization, were dislodged by gentle spraying with a pipet.

Fixation and Permeabilization

Soak in slide holder 15 min in 4% paraformaldehyde, pH 7.4. Rinse in water. Permeabilized 5 min in 1×PBS/0.5% Triton X-100. Then soak 2 times in 2×SSC buffer, with mild shaking. Then soak 5 min each in 70% ethanol, 90% ethanol, and then 100% ethanol. The slides are then dried overnight at room temperature.

Prehybridization

Install gaskets (Bio-Rad, Hercules, Calif.) around cells on slides. Add solution of 0.25 μl BSA (10 mg/mL; Promega, Madison, Wis.), 2.5 μl sonicated herring sperm DNA (10 mg/mL; Promega, Madison, Wis.), and add hybridization buffer (1.5×SSC, 5 mM EDTA, 0.2% Tween 20) to 25 μl per slide. Cover gaskets with plastic covers (Bio-Rad, Hercules, Calif.), incubate in slide moat (Boekel Scientific, Feasterville, Pa.) at 37° C. for 1 hr. Wash 3 times, 5 min each, in 2×SSC, rinse in water, dry.

Hybridization

1. Mix (per 25 μl reaction) 5 μl T-probe (10 pm/μl; 10 μMolar) and 5 μl extension (10 pm/μl; 10 μMolar) to a concentration of 2 μMolar each in hybridization buffer (1.5×SSC, 5 mM EDTA, 0.2% Tween 20), heat 3 min in 0.2 mL tube in thermal cycler at 96° C.
2. Place gasket around cells, pipet 25 μl of mixture per slide onto slide, cover.
3. Incubate in slide moat from 65° C. to 45° C. for 2 hr, allowing the slide moat to cool to 60° C. and stopping the cooling for 0.5 hr, to 55° C., stopping the cooling for 0.5 hr, and then to 50° C., stopping the cooling for 0.5 hr, and then to 45° C.
4. Wash 2 times in 2×SSC buffer at room temperature, with agitation.

Ligation of Probe

1. Make a mix of (per 25 μl reaction) 2.5 μl ligase buffer (10×; Roche Diagnostics, Indianapolis, Ind.), 4 units T4 ligase (1 U/μl; Roche Diagnostics, Indianapolis, Ind.), 2.5 μl 1% Tween 20 (Sigma-Aldrich, St. Louis, Mo.) with 600 mM NaCl, 0.3 μl BSA (10 mg/mL; Promega, Madison, Wis.), and water.
2. Place gasket around cells and pipet 25 μl of solution onto slide, cover.
3. Incubate in slide moat at 37° C. for 1.5 hr.
4. Wash 2 times for 5 min each in 2×SSC at 60° C. Rinse water, dry.

Circle Annealing and Ligation

1. Mix 2.5 μl circularizable probe (10 pmole/μl; 10 μMolar) in water.
2. Heat in 0.2 mL tube in thermal cycler 95° C. 3 min.
3. Mix 4 units T4 ligase, 2.5 μl ligase buffer, 2.5 μl Tween 20 with 600 mM NaCl, 0.3 μl BSA, add circle mixture, and add water to a total of 25 μl/reaction.
4. Place gaskets around cells on slide, pipet 25 μl of solution onto slide, cover.
5. Anneal and ligate in slide moat for 2 hr from 50° C. to 40° C. Stop for 1 hr at 45° C., and then continue cooling to 40° C.
6. Wash 2 times for 5 min each in 2×SSC at 40° C., rinse water, dry.

Rolling Circle Amplification

1. Mix (per 25 μl reaction) 2.5 μl dNTPs (1 mM), 2.5 μl phi 29 buffer (10×; Epicentre, Madison, Wis.), 0.2 μl phi29 (0.1 μg/μl; Epicentre, Madison, Wis.), 2.0 μl single-stranded binding protein (2 mg/mL; Epicentre, Madison, Wis.), 1 μl biotin-16-dUTP (1 mM; Roche Diagnostics, St. Louis, Mo.), and water. Place gasket on slide around cells, and pipet 25 μl of mixture onto slide. Cover.

2. Incubate in slide moat at 30° C. for 1 hr.
3. Wash 3 times for 5 min each in 0.5% Triton X-100 in 1×PBS with agitation.

Visualization

1. Pipet 25 μl of oligo/fluor (10 pm/μl) solution onto cells on slide.
2. Place coverslip over cells on slide, incubate in slide moat at 37° C. for 15 min, with water in wells of slide moat to prevent drying of slide.
3. Wash 2 times for 5 min each in 0.5% Triton X-100/1×PBS with agitation. Rinse water, dry.
4. Pipet 200 μl PNM block (0.1M phosphate buffer (pH 8.0), 0.1% Nonidet P 40 substitute, 5% nonfat dry milk, 0.02% sodium azide) onto slide, incubate at 37° C. for 5 min, in humid conditions (e.g., in tissue culture incubator).
5. Pipet 100 μl 1:100 streptavidin (Invitrogen, Eugene, Oreg.) solution onto the PNM block. Incubate for 30 min at 37° C. in humid conditions (e.g., in cell culture incubator).
6. Wash 2 times for 5 min each in PN (0.1M phosphate buffer (pH 8.0), 0.1% Nonidet P 40 substitute) buffer. Rinse in water, dry.
7. Pipet 15 μl ProLong Gold anti-fade reagent with DAPI (Invitrogen, Eugene, Oreg.) onto cells on slide; visualize under fluorescence microscope.

Results

The probe was detected on H460 cells, to detect CcO4-1 expression. A number of negative controls were also employed, in which it was systematically left out of the reaction mixture, one by one, the circularizable probe, the extension, the polymerase, the ligase, and the T-probe. There was no FITC signal in any of the negative controls.

*Drosophila melanogaster* cells were used as a negative control. While there is a DAPI-stained nucleus visible, there is no FITC signal, indicating that the probes were washed away in the washing step. Thus, the probe does not bind non-specifically.

Discussion

It appears that rolling circle amplification has not yet achieved the high hopes generated at the time of its introduction as a technique in molecular biology applications. Herein it is employed in a design for a hybridization probe so that the benefits of both probe ligation and rolling circle amplification can be realized together.

Probe ligation with a subsequent washing step ensures that not one but two recognition sequences must anneal in order to produce a signal. While annealing to the wrong target is a common occurrence, it is very unlikely that two recognition sequences will strongly anneal to two contiguous wrong sequences, enabling their ligation after a washing step.

Rolling circle amplification has been shown to increase signal as much as 1000-fold when a fluorescent signal is attached to the amplified product. The problem with rolling circle appears to be that when the rolling circle reaction proceeds along a padlock probe whose two ends anneal to adjacent target sequences, its progress is impeded by interference from the target.

The technique described herein combines probe ligation with rolling circle amplification, but it separates the two processes in space, so that there is no steric hindrance to interrupt the progress of the strand-displacing polymerase.

The probe technology described herein finds uses beyond detecting CcO4-1 and CcO4-2 expression singly. It can easily be multiplexed, so that, for example, both CcO4-1 and CcO4-2 mRNA could be detected at the same time. In order to multiplex the assay, what would be required is a separate probe that would incorporate a recognition sequence for the new target, a stem that would anneal with a new circularizable probe, and a linker region in the circularizable probe that would after amplification provide a target for fluors that are of a different color.

While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

All publications, patents and patent applications listed herein are herein incorporated by reference.

DOCUMENTS

American Cancer Society (2002) Cancer facts and figures 2002.

Acin-Perez et al.: (2003) An intragenic suppressor in the cytochrome c oxidase I gene of mouse mitochondrial DNA. Hum Mol Genet 12 329-39.

Archer et al.: (2002) The mechanism(s) of hypoxic pulmonary vasoconstriction: potassium channels, redox O(2) sensors, and controversies. News Physiol Sci 17 131-7.

Arnold et al.: (1999) The intramitochondrial ATP/ADP-ratio controls cytochrome c oxidase activity allosterically. FEBS Lett 443 105-8.

Avanzo et al.: (2004) Increased susceptibility to urethane-induced lung tumors in mice with decreased expression of Connexin 43. Carcinogenesis.

Barros et al.: (2001) Hypoxic metabolic response of the golden-mantled ground squirrel. J Appl Physiol 91 603-12.

Baty et al.: (2002) Detection of oxidant sensitive thiol proteins by fluorescence labeling and two-dimensional electrophoresis. Proteomics 2 1261-6.

Boehle et al.: (2002) Wortmannin inhibits growth of human non-small-cell lung cancer in vitro and in vivo. Langenbecks Arch Surg 387 234-9.

Burke et al.: (1998) Structure/function of oxygen-regulated isoforms in cytochrome c oxidase. J Exp Biol 201 (Pt 8) 1163-75.

Cantley: (2002) The phosphoinositide 3-kinase pathway. Science 296 1655-7.

Chandel et al.: (2000) Cellular oxygen sensing by mitochondria: old questions, new insight. J Appl Physiol 88 1880-9.

Cuezva et al.: (1997) Mitochondrial biogenesis in the liver during development and oncogenesis. J Bioenerg Biomembr 29 365-77.

Epstein et al.: (1978) A theoretical analysis of the barometric method for measurement of tidal volume. Respir Physiol 32 105-20.

Esamai: (1998) Relationship between exposure to tobacco smoke and bronchial asthma in children: a review. East Afr Med J 75 47-50.

Ferguson-Miller et al.: (1976) Correlation of the kinetics of electron transfer activity of various eukaryotic cytochromes c with binding to mitochondrial cytochrome c oxidase. J Biol Chem 251 1104-15.

Gnaiger et al.: (1998) Mitochondrial oxygen affinity, respiratory flux control and excess capacity of cytochrome c oxidase. J Exp Biol 201 (Pt 8) 1129-39.

Green et al.: (2003) Management of asthma in adults: current therapy and future directions. Postgrad Med J 79 259-67.

Grossman et al.: (1997) Nuclear genes for cytochrome c oxidase. Biochim Biophys Acta 1352 174-92.

Gyuris et al.: (1993) Cdi1, a human G1 and S phase protein phosphatase that associates with Cdk2. Cell 75 791-803.

Hirsch et al.: (1997) Prevention and early detection of lung cancer-clinical aspects. Lung Cancer 17 163-74.

Hüttemann et al.: (2003a) Cytochrome c oxidase of mammals contains a testes-specific isoform of subunit VIb—the counterpart to testes-specific cytochrome c? Mol Reprod Dev 66 8-16.

Hüttemann et al. (2001) Mammalian subunit IV isoforms of cytochrome c oxidase. Gene 267 111-23.

Hüttemann et al.: (2003b) A third isoform of cytochrome c oxidase subunit VIII is present in mammals. Gene 312 95-102.

Jacky: (1980) Barometric measurement of tidal volume: effects of pattern and nasal temperature. J Appl Physiol 49 319-25.

Joad et al.: (2004) Passive smoke effects on cough and airways in young guinea pigs: role of brainstem substance P. Am J Respir Crit Care Med 169 499-504.

Kadenbach et al.: (2004) The possible role of cytochrome c oxidase in stress-induced apoptosis and degenerative diseases. Biochim Biophys Acta 1655 400-8.

Kolonin et al.: (2000) Interaction mating methods in two-hybrid systems. Methods Enzymol 328 26-46.

Korshunov et al.: (1997) High protonic potential actuates a mechanism of production of reactive oxygen species in mitochondria. FEBS Lett 416 15-8.

Kosower et al. (1995) Diamide: an oxidant probe for thiols. Methods Enzymol 251 123-33.

Li et al.: (2002) Lung pathology in platelet-derived growth factor transgenic mice: effects of genetic background and fibrogenic agents. Exp Lung Res 28 507-22.

Lin et al.: (2001) Overexpression of phosphatidylinositol 3-kinase in human lung cancer. Langenbecks Arch Surg 386 293-301.

Lundblad et al.: (2002) A reevaluation of the validity of unrestrained plethysmography in mice. J Appl Physiol 93 1198-207.

Malkinson: (1989) The genetic basis of susceptibility to lung tumors in mice. Toxicology 54 241-71.

Miller et al.: (2003) Induction of a high incidence of lung tumors in C57BL/6 mice with multiple ethyl carbamate injections. Cancer Lett 198 139-44.

Napiwotzki et al. (1997) ATP and ADP bind to cytochrome c oxidase and regulate its activity. Biol Chem 378 1013-21.

Ng et al.: (2004) Protein-DNA footprinting by endcapped duplex oligodeoxyribonucleotides. Nucleic Acids Res 32 e107.

Nilsson et al.: (2002) Real-time monitoring of rolling-circle amplification using a modified molecular beacon design. Nucleic Acids Res 30 e66.

Pedersen: (1978) Tumor mitochondria and the bioenergetics of cancer cells. Prog Exp Tumor Res 22 190-274.

Robinson-White et al.: (2002) Protein kinase A signaling: "cross-talk" with other pathways in endocrine cells. Ann N Y Acad Sci 968 256-70.

Rodriguez-Enriquez et al.: (1998) Intermediary metabolism of fast-growth tumor cells. Arch Med Res 29 1-12.

Ryan et al.: (1987) KRAS2 as a genetic marker for lung tumor susceptibility in inbred mice. J Natl Cancer Inst 79 1351-7.

Santillan et al. (2003) A meta-analysis of asthma and risk of lung cancer (United States). Cancer Causes Control 14 327-34.

Schuller et al.: (2004) Neuroendocrine lung carcinogenesis in hamsters is inhibited by green tea or theophylline while the development of adenocarcinomas is promoted: implications for chemoprevention in smokers. Lung Cancer 45 11-8. SEER: Cancer facts and statistics. SEER, 1998.

Siddiq et al.: (2004) Increased osteonectin expression is associated with malignant transformation and tumor associated fibrosis in the lung. Lung Cancer 45 197-205.

Sodhi et al.: (2001) Hypoxia and high glucose cause exaggerated mesangial cell growth and collagen synthesis: role of osteopontin. Am J Physiol Renal Physiol 280 F667-74.

Suh et al.: (1999) Cell transformation by the superoxide-generating oxidase Mox1. Nature 401 79-82.

Tsukihara et al.: (1996) The whole structure of the 13-subunit oxidized cytochrome c oxidase at 2.8 A. Science 272 1136-44.

Vaupel et al.: (1989) Blood flow, oxygen and nutrient supply, and metabolic microenvironment of human tumors: a review. Cancer Res 49 6449-65.

Villani et al. (1998) Low reserve of cytochrome c oxidase capacity in vivo in the respiratory chain of a variety of human cell types. J Biol Chem 273 31829-36.

von Wangenheim et al.: (1998) Control of cell proliferation by progress in differentiation: clues to mechanisms of aging, cancer causation and therapy. J Theor Biol 193 663-78.

Wong-Riley: (1979) Changes in the visual system of monocularly sutured or enucleated cats demonstrable with cytochrome oxidase histochemistry. Brain Res 171 11-28.

Yamamoto et al.: (1977) Fluorometric studies on the light chains of skeletal muscle myosin. I. Effects of temperature, ionic strength, divalent metal ions, and nucleotides. J Biochem (Tokyo) 82 747-52.

You et al. (1992) Parental bias of Ki-ras oncogenes detected in lung tumors from mouse hybrids. Proc Natl Acad Sci USA 89 5804-8.

Zhong et al.: (2003) A strategy for constructing large protein interaction maps using the yeast two-hybrid system: regulated expression arrays and two-phase mating. Genome Res 13 2691-9.

The invention claimed is:

1. A method to detect a messenger ribonucleic acid (mRNA) sequence comprising:
   a) annealing a first probe and a second probe to at least a portion of the mRNA, wherein the first and second probes do not comprise the same nucleotide sequence, wherein each probe sequence is complimentary to at least a portion of the mRNA and the second probe is a T-shaped probe having 1) a probe sequence complementary to at least a portion of the mRNA sequence and 2) a rolling circle amplification primer that is linked to an internal reactive group of the probe sequence of the second probe so as to provide physical separation of probe ligation and rolling circle amplification, said probe-connected rolling circle primer comprising a circle recognition sequence;
   b) concatenating the two annealed probes with a ligase to yield a ligated annealed probe and removing unligated probe from the mRNA sequence, wherein the ligated probe does not circularize;
   c) annealing a single stranded amplification circle to the circle recognition sequence of the ligated probe, wherein the single stranded amplification circle codes for a recognition sequence for an oligonucleotide to which a detectable molecule is attached;
   d) generating a plurality of copies of the circle containing the oligonucleotide recognition sequence with a strand replacement polymerase;
   e) annealing the oligonucleotide to at least one of the oligonucleotide recognition sequences; and
   f) detecting the presence of the detectable molecule, wherein the presence of the detectable molecule correlates with the presence of the mRNA.

2. The method of claim 1, wherein the ligated probes span an exon-exon junction.

3. The method of claim 1, wherein the mRNA sequence is human.

4. The method of claim 1, wherein the first or second probe is 5' phosphorylated.

5. The method of claim 4, wherein the first or second probe further comprises 3-carbon spacer or a di-deoxy nucleotide at the 3'-end.

6. The method of claim 1, wherein the second probe comprises a 6-carbon linker to an internal thymine nucleotide.

7. The method of claim 1, wherein the detectable molecule is a fluorophore.

8. The method of claim 1, wherein the detectable molecule is Oregon Green or Texas Red.

9. A method to detect a messenger ribonucleic acid (mRNA) sequence comprising:
   a) annealing a first probe and a second probe to at least a portion of the mRNA, wherein the first and second probes do not comprise the same nucleotide sequence, wherein the first or second probe further comprises a 3-carbon spacer or a di-deoxy nucleotide at the 3'-end, wherein each probe sequence is complimentary to at least a portion of the mRNA and the second probe is a T-shaped probe having 1) a probe sequence complementary to at least a portion of the mRNA sequence and 2) a rolling circle amplification primer that is linked to an internal reactive group of the probe sequence of the second probe so as to provide physical separation of probe ligation and rolling circle amplification, said probe-connected rolling circle primer comprising a circle recognition sequence;
   b) concatenating the two annealed probes with a ligase to yield a ligated annealed probe and removing unligated probe from the mRNA sequence;

c) annealing a single stranded amplification circle to the circle recognition sequence of the ligated probe, wherein the single stranded amplification circle codes for a recognition sequence for an oligonucleotide to which a detectable molecule is attached;
d) generating a plurality of copies of the circle containing the oligonucleotide recognition sequence with a strand replacement polymerase;
e) annealing the oligonucleotide to at least one of the oligonucleotide recognition sequences; and
f) detecting the presence of the detectable molecule, wherein the presence of the detectable molecule correlates with the presence of the mRNA.

* * * * *